(12) United States Patent
Riordan et al.

(10) Patent No.: US 6,813,009 B2
(45) Date of Patent: Nov. 2, 2004

(54) DETECTION OF METABOLIC DYSFUNCTIONS USING FLUORESCENCE EMISSION FROM SERUM

(75) Inventors: Hugh D. Riordan, Wichita, KS (US); Paul Rillema, Wichita, KS (US); Nina Mikarova, Wichita, KS (US)

(73) Assignee: The Center for the Improvement of Human Functioning, International, Inc., Wichita, KS (US)

( * ) Notice: Subject to any disclaimer, the term of this patent is extended or adjusted under 35 U.S.C. 154(b) by 147 days.

(21) Appl. No.: 09/956,504

(22) Filed: Sep. 18, 2001

(65) Prior Publication Data

US 2003/0137649 A1 Jul. 24, 2003

(51) Int. Cl.[7] .................. G01N 33/48; G01N 21/00; G01J 3/00; G01J 3/40; B01D 57/02
(52) U.S. Cl. .................. 356/39; 356/300; 356/303; 356/337; 356/451; 356/456; 204/450; 204/451
(58) Field of Search ......................... 356/39, 300, 303, 356/337, 451, 456; 204/450, 451

(56) References Cited

U.S. PATENT DOCUMENTS 5,784,162 A * 7/1998 Cabib et al.
6,537,432 B1 * 3/2003 Schneider et al.

OTHER PUBLICATIONS

Wolfbeis et al ("Mapping of the total fluorescence of human blood serum as a new method for its characterization" —Analytica Chimica Acta, 167 (1985) p. 203–215).*

Gillenwater, et al. "Noninvasive Diagnosis of Oral Neoplasia Based on Fluorescence Spectroscopy and Native Tissue Autofluorescense" *Arch Otolrygnol Head Neck Surg* vol. 124, Nov. 1998, pp. 1251–1258.

Hubmann, et al. "Ultraviolet Fluorescence of Human Sera: I. Sources of Characteristic Differences in the Ultraviolet Fluorescence Spectra of Sera from Normal and Cancer–Bearing Humans" *Clin. Chem.*36/11, 188–1883 (1990).

Leiner, et al. "Fluorescence Topography in Biology. III: Characteristic Deviations of Tryptophan Fluorescence in Sera of Patients with Gynecological Tumors" *Clinical Chemistry* vol. 32, No. 10, 1986 pp. 1974–1978.

Lohman, et al. "Native Fluorescence of Plasma from Patients with Acute Leukemias" *Naturwissenschaften* 75 (1988) pp. 365–367.

Mabuchi, et al. "Liquid–Chromatographic Profiling of Endogenous Fluorescent Substances in Sera and Urine of Uremic and Normal Subjects" *Clinical Chemistry* vol. 29, No. 4, 1983, pp. 675–677.

Warner, et al. "Multicomponent Analysis in Clinical Chemistry by Use of Rapid Scanning Fluorescence Spectroscopy" *Clinical Chemistry* 22/9, 1483–1492 (1976).

Wolfbeis, et al. "Mapping of the Total Fluorescence of Human Blood Serum as a New Method for Its Characterization" *Analytica Chimica Acta* 167, (1985) pp. 203–215.

Yang, et al. "Fluorescence Spectroscopy as a Photonic Pathodlgy Method for Detecting Colon Cancer" *Lasers in the Life Sciences* 6(4), 1995, pp. 259–276.

Yang, et al. "Fundamental Differences of Ecitation Spectrum between Malignant and Benigh Breast Tissues" *Photochemistry and Photobiology* 1997, 66(4): pp. 518–522.

* cited by examiner

*Primary Examiner*—Frank G. Font
*Assistant Examiner*—Khaled Brown
(74) *Attorney, Agent, or Firm*—Knobbe, Martens, Olson & Bear, LLP

(57) ABSTRACT

Serum emission can be used as the first test to detect metabolic disorders in mammals. When changes in emission of the serum from patients with different pathological conditions were characterized, a difference was seen for patients with diseases such as cancer, thyroid disorder, arthritis, diabetes, coronary artery disease (CAD), hypertension, CFS (chronic fatigue syndrome), and fibromyalgia. The level of emission was enhanced or diminished and correlated with the level of energy metabolism and the level of metabolic rate. The method can also be used for risk assessment, to identify whether a treatment is working or to follow the course of a treatment, and to identify changes in energy levels due to stress, etc.

31 Claims, 13 Drawing Sheets

DETECTION OF METABOLIC DYSFUNCTIONS USING FLUORESCENCE EMISSION FROM SERUM

FIELD OF THE INVENTION

Aspects of the invention relate to methods of detection of metabolic dysfunctions using fluorescence emission from serum.

BACKGROUND OF THE INVENTION

Over the past several years, fluorescence spectroscopy, a method that is several orders of magnitude more sensitive and more selective than absorption-based techniques, has been used to characterize physicochemical properties of biomolecules that exhibit fluorescence in cells, tissues and in serum. Consequently, fluorescence spectroscopy of biomolecules has been used to characterize cell metabolic pathways and to discriminate pathological conditions of cells, tissues and organs from their normal state. Previously, native fluorescence emission and excitation spectra of infected human keratinocytes, carcinoma cells, and normal human keratinocytes were measured and were shown to differ in the intracellular metabolic state of NADH. It was suggested that the observed differences were due to an increased proportion of bound mitochondrial NADH in the cancer and virus-infected cells.

In the field of diagnostic oncology, studies indicate that native fluorescence properties of tissue can be used to distinguish normal from malignant conditions in breast, cervix, colon, and bronchus samples. Measurements of emission intensity or spectral ratios of emission intensity (for example at 340 and 440 nm) under UV light excitation were shown to statistically differentiate normal from malignant tissues. The analysis of excitation spectra, monitored at the emitting wavelength (340 nm), indicated distinct differences between normal and tumor tissues.

In a series of studies, a fluorometric screening method was established for the analysis of the emission of serum to detect patients with tumors and chronic diseases. The ultra-violet fluorescence emission spectra of sera (mostly protein content) from healthy persons and of sera from cancer patients, frequently exhibited different curve shapes. Thus, to differentiate between normal sera and sera from patients suffering from neoplastic diseases, the authors analyzed emission properties in the near-ultraviolet region of the spectrum. The method developed was based on expressing the measurements obtained by the fluorescence intensity at 365 nm as a percentage of the fluorescence intensity at 337 nm. Compared with ultraviolet fluorescence emission (excitation 287 nm) of sera from healthy persons, the emission spectra of tumor sera were characterized by two regions with minor fluorescence intensities at 300 m and 340 nm and by one region of higher intensity near 325 nm. To account for the differences, the authors focused on human serum proteins, the material mainly responsible for the intrinsic fluorescence of sera in the UV spectral region. The main components that influenced the fluorescence intensity ratio were albumin and alpha-2 globulins. According to these authors, the effect may be produced by differences in the relative protein composition, which are frequently symptoms in malignancies, or tumor associated metabolites may bind to serum proteins and alter their fluorescence emission.

In addition to the complexity of observing differences in emission from different fractions in serum, fluorescence in native serum can be attributed to a variety of molecules including tryptophan (trp), tyrosine (tyr), phenylalanine (phe), NADH, pyridoxal phosphate, bilirubin, flavin-adenine dinucleotide (FAD) and others. The fluorescence associated with these molecules is defined by their concentration and distribution as well as the photo-physicochemical properties of their environment.

These previous results suggest that serum emission can be used to identify metabolic dysfunctions in humans and other animals. However, no such technique has been developed. Therefore, a study was initiated to identify a method to detect metabolic dysfunctions by fluorescence in human sera. The results reported here clearly allow one to differentiate normal from abnormal metabolic behavior in human functioning and may lead to improvement of human functioning through early detection of such disorders.

SUMMARY OF THE INVENTION

A method was identified which allows one to detect metabolic dysfunctions by fluorescence in human sera. One embodiment of this is a method for the diagnosis of a disease of metabolic dysfunction, by obtaining a sample of serum from a patient who has fasted for at least about 8 hours; irradiating the sample at an irradiation wavelength from about 300 to about 340 nm; measuring the serum emission at a wavelength from about 300 to about 600 nm; and diagnosing the presence of a metabolic dysfunction by an increased or decreased emission in comparison to an average emission at the wavelength of serum of a plurality of normal healthy volunteers.

The emission wavelength can be anywhere from about 330 to about 550, preferably, 370 to about 550, preferably from about 425 to about 500, preferably from about 470 to about 500, preferably from about 460 to about 490. Alternatively a plurality of irradiation wavelengths is used. The plurality of irradiation wavelengths can be selected from the group consisting of: 315, 325 and 340.

In one embodiment, the metabolic dysfunction is cancer and the serum emission is reduced. In a further embodiment, the patient with cancer has more than a 5% decrease in the level of serum emission. Alternatively, the patient with cancer has more than a 10% decrease in the level of serum emission. Alternatively, the patient with cancer has more than a 20% decrease in the level of serum emission. The patient with cancer may have a decrease in the serum emission from about 5% to about 60%. Alternatively, the decrease in the serum emission is from about 10% to about 50%.

In a further embodiment, the metabolic dysfunction is hypothyroidism and the serum emission is reduced. Alternatively, the metabolic dysfunction is hyperthyroidism and the serum emission is increased. Alternatively, the metabolic dysfunction is diabetes and the serum emission is reduced. In a further embodiment, the metabolic dysfunction is fatigue and the serum emission is reduced. Alternatively, the metabolic dysfunction is coronary artery disease (CAD) and the serum emission is reduced.

In a further embodiment, the sample is irradiated at both 325 nm and 340 nm. Preferably, the sample is irradiated at the wavelength which allows the best resolution for NAD(P)H.

In one embodiment, the cancer is selected from the group consisting of: breast cancer, lung cancer, colon cancer, prostate cancer and leukemia.

A further embodiment is a method for analysis of the effectiveness of a treatment, by: obtaining a first sample of serum from a patient before the treatment, wherein the patient has fasted for at least about 8 hours prior to obtaining the first sample; irradiating the first sample at an irradiation wavelength from about 300 to about 340 nm; measuring the serum emission at an emission wavelength from about 300 to about 600 nm; obtaining a second sample of serum from a patient after the treatment, wherein said patient has fasted for at least about 8 hours prior to obtaining the first sample; irradiating the second sample at an irradiation wavelength from about 300 to about 340 nm; measuring the serum emission at an emission wavelength from about 300 to about 600 nm; and diagnosing the effectiveness of the treatment by an increased or decreased emission in the second sample relative to the first sample. In one embodiment, the treatment is a treatment for cancer and the treatment is diagnosed as being effective by an increased emission.

DETAILED DESCRIPTION OF THE INVENTION

Figure 1:
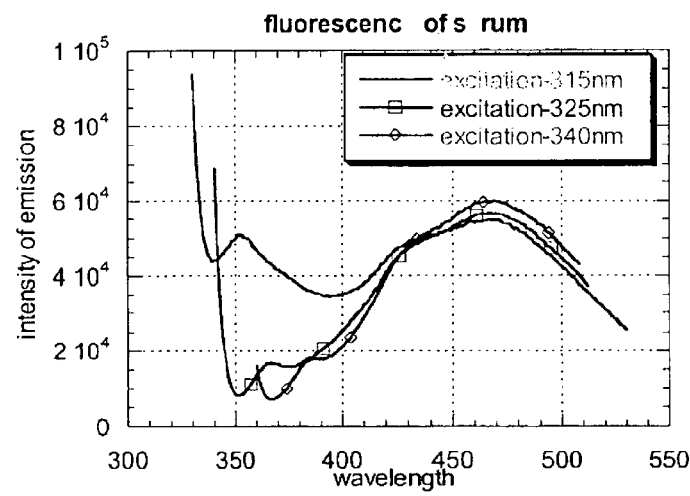
FIG. 1 is the average fluorescence emission spectra for the excitation wavelengths 315, 325 and 340 nm for healthy volunteers' serum.

Serum emission can be used as the first test to detect metabolic disorders in mammals. When changes in emission of the serum from patients with different pathological conditions are characterized, a difference is seen for patients with diseases such as cancer, thyroid disorder, arthritis, diabetes, coronary artery disease (CAD), hypertension, CFS (chronic fatigue syndrome), and fibromyalgia. The level of emission is enhanced or diminished and correlates with the level of energy metabolism and the level of metabolic rate. The method can also be used for risk assessment, to identify whether a treatment is working or to follow the course of a treatment, and to identify changes in energy levels due to stress, etc.

The method of the preferred embodiment allows the identification of any metabolic disorder or any disease associated with a metabolic disorder by a measurement of the serum emission. The value obtained can be compared to a known normal value or can be compared to a patient's known value. The method can be used to diagnose or identify pre-disposition to a metabolic disorder or to a disease which is associated with a metabolic disorder. The method can alternatively or additionally be used to follow the course of a treatment or the course of the disease.

The method may be used to analyze any metabolic disorder or any disease which is associated with a metabolic disorder. Diseases which are known to be metabolic disorders or associated therewith include, but are not limited to: cancer, thyroid disorders, fatigue and arthritidies, and coronary diseases. However, research reveals the presence of metabolic factors in many new and old diseases and it is envisioned that the method can be used for any of the newly identified metabolic disorders.

The method involves isolating serum from a patient, obtaining a fluorescence spectrum of that serum, and comparing that fluorescence spectrum to one obtained for normal serum or to a previous sample.

The serum sample can be isolated by any method known to one of skill in the art. However, vitamins and drugs or pharmaceuticals are known to interfere with the fluorescence. Therefore, these substances are removed from the serum sample. Alternatively, a fasting serum sample is taken where the patient has fasted for enough time that these substances are no longer in the blood. Typically this takes from 2 to 24 hours. However, preferably, the fasting sample is taken after 3 hours, more preferably 4 hours, even more preferably 5 hours, 6 hours, 7 hours or 8 hours. However, typically fasting sample are taken after 10 to 12 hours of fasting. Alternatively, such substances can be removed from the serum using methods known to one of skill in the art. In one embodiment, the serum is diluted to allow the best measurement of the fluorescence. The amount of dilution may depend upon the specific spectrofluorometer or it may be affected by the patient's serum, or the method of obtaining the serum sample. However, if the serum is diluted in a buffer, the fluorescence of the buffer is subtracted from that of the serum sample. In one embodiment, the serum is diluted from about 1:1 to about 1:100. In a further embodiment, the serum is diluted from about 1:2 to about 1:20, including, but not limited to, 1:3, 1:4, 1:5, 1:6, 1:7, 1:8, 1:9, 1:10, 1:11, 1:12, 1:13, 1:14, 1:15, 1:16, 1:17, 1:18, and 1:19. In a further embodiment, the serum is diluted from about 1:4 to about 1:10.

The fluorescence spectrum may be obtained using any method known to one of skill in the art. In one embodiment, an excitation wavelength (or irradiation wavelength) in the range of about 300 to 340 nm is used. In a further embodiment, an irradiation wavelength of about 315 to about 340 nm is used. The excitation wavelength was chosen to exclude the effect of protein emission, which has a very intense peak in the range of 280–320 nm. Typically, the fluorescence emission spectra for the excitation wavelengths 315, 325 and 340 nm are taken. However, any wavelengths within the ranges would be applicable. In addition, any wavelength which allows for the measurement of NAD(P)H (or NADH) in blood can be used. In a further embodiment more than one wavelength is used and more than one spectrum is analyzed. In a further embodiment, the more than one wavelength includes one or more of excitation wavelengths 315, 325 and 340 nm. For example, irradiation wavelengths of 315, 325 and 340 nm are taken and the results of each is analyzed.

Excitation of serum samples can occur at various wavelengths in the range of 315–340 nm or at all wavelengths simultaneously. Thus, in a further embodiment, all of the wavelengths simultaneously are used. A slice of light using filters from 315 nm to 340 nm from an irradiation lamp which gives out a much broader range spectrum. For example, just purple light selected from the solar spectrum is used or red light, etc.

In one embodiment, the emission wavelengths are in the range of about 300 to about 600 nm. In a further embodiment, emission wavelengths of from about 350 to about 500 nm is used, including, but not limited to, 360, 370, 380, 390, 400, 410, 420, 430, 440, 450, 460, 470, 480, and 490. In a further embodiment, an emission wavelength of from about 370 to about 550 is used. In a further embodiment, an emission wavelength of from about 425 to about 500 is used. In a further embodiment, an emission wavelength of from about 470 to about 500 is used. In a further embodiment, an emission wavelength of from about 460 to about 490 is used. In a further embodiment, the emission wavelength which measures NAD(P)H (or NADH) in blood is used.

Because emission of serum can occur at various wavelengths, collection of emitted light can occur at one wavelength or all of the wavelengths can be collected simultaneously. Thus, in a further embodiment, all of the emitted light is collected rather than one specific wavelength, such as 470 nm. The summative emission of light provides more intensity since it is a sum of the emission intensity at each wavelength but gives the same information. For example, the area under the emission curve is added to obtain a value for the amount of emission.

In one embodiment, the fluorescence spectrum of the solvent which the serum is diluted in is measured and that value is subtracted from the value obtained for the serum sample.

In a further embodiment, the same measurements are taken for healthy volunteer's serum to provide a normal value. This value may be affected by the instrument used and may require a new control to be performed. This is because the intensity level obtained from blood emission will be affected by a number of factors, including the Fluorimeter or instrument used, the light source, the slit width, and many other factors. Therefore, it is to be understood that the method can still be used with any type of instrument.

For the purpose of diagnosis or for an initial screening test, the measurement of the serum sample will typically be compared to a normal value. However, if the course of disease or a treatment is being followed, the measurement of the serum sample may be compared to an initial measurement and any others which follow. This would allow one to determine if the serum fluorescence is increasing or decreasing with treatment and if it is getting closer to a normal value.

Alternatively, the method may be used at each yearly physical for a normal or diseased patient to see a trend or to look for unusual changes in the measurements. A trend upward or downward or an unusual change in the emission upward or downward could signal a metabolic disorder, or could be used as a sign that the patient needs further diagnosis.

When diagnosing the presence of Cancer (or an alternative metabolic disorder), a reduction from normal serum emission of from about 5% to about 90% signals the presence of cancer or an alternative metabolic disorder. In a further embodiment, a reduction of from about 10% to about 75% signals Cancer, including 15%, 25%, 35%, 40%, 45%, 55%, 65%, 70%, 80%, and 85%. In a further embodiment, a reduction of from about 20% to about 50% signals Cancer or a metabolic disorder. In a further embodiment, a reduction of from about 10% to about 50% signals Cancer or a metabolic disorder. In a further embodiment, a reduction of from about 30% to about 50% signals Cancer or a metabolic disorder.

In the examples which follow, patients with known disorders were analyzed as to serum emission. The results were used to devise a test for these disorders. In Examples 1–3 the methods of preparation of the samples and measurement by spectroscopy are explained.

EXAMPLE 1

Preparation of Samples

Baseline, normal blood samples were obtained from healthy staff volunteers. The experimental samples of serum were obtained from patients which were clinically diagnosed with cancer or different types of metabolic diseases. Serum was separated from blood by centrifugation at 3500 rpm for 15 minutes. Most serum samples were obtained from individuals who had fasted overnight to exclude the effect of fluorescence emission of drugs and vitamins. Some samples were stored frozen at $-20°$ C. for up to one month and measured after this period. To analyze the effect of using frozen serum as a sample, several samples from healthy volunteers were measured before and after frozen storage and it was shown that the emission of the serum did not change after one month.

All specimens were diluted with PBS (Phosphate Buffered Saline) using a ratio of 1:20 to measure the emission in the range of absorption less than 0.1 at the excitation wavelength. This allowed measuring the fluorescence in the region where there is a linear relationship between fluorescence and concentration. For calibrating the instruments, several standards were used: rhodamine B, [Ru(bpy)$_3$]$^{2+}$ in EtOH:MeOH (4:1) solution, and a composite of normal serum solutions from several staff volunteers.

EXAMPLE 2

Procedure for Measurements

For each specimen and solvent, the fluorescence spectra were run using a SPEX spectrofluorometer (sensitivity 4000:1, double-grating spectrophotometers). The light source was a 125W xenon lamp. The device had two double-grating monochromators, one for excitation and another for emission. The emitted photons were measured with a Hamamatsu R928 photomultiplier tube. For measurements, the solutions were placed in quartz cells, and the measurements were obtained with a 90-degree angle between the beams of excitation and the emission light path. For the excitation scans, the range of wavelengths used was 315–340 nm and for emission 330–600 nm. The background curves for the solvent (PBS) were measured each time before measurements of the diluted serum. The fluorescence spectra of solvent was subtracted from the fluorescence spectra of serum to remove background effects.

EXAMPLE 3

Spectroscopy

Irradiation of the samples at wavelengths in the range of 300–340 nm gave rise to emission in the 350–600 nm region coinciding with the respective absorption and emission of NAD(P)H, along with other contributing molecules. The excitation wavelength was chosen to exclude the effect of protein emission, which has a very intense peak in the range of 280–320 nm. The average fluorescence emission spectra for the excitation wavelengths 315, 325 and 340 nm for healthy volunteers' serum are shown in FIGS. 1, and 19–23. The excitation of samples at wavelengths 325 and 340 nm gave better resolution for NAD(P)H, the principle emitting contributor, and other fluorophore emissions in the visible range since tryptophan, which absorbs at 315 nm, does not have any significant absorption in this range (FIG. 1).

EXAMPLE 4

The Method Used for Estimating the Level of the Serum Emission for Patients with Metabolic Disorders The fluorescence emission curves for healthy volunteers were measured to establish a baseline for the normal series. Only the serum from fasting volunteers (40 curves) was used for the analysis of emission range variation, because the analysis from non-fasting volunteers showed a significant influence from vitamins (especially Vitamin B$_6$) and drug uptake on the level of serum emission in UV-visible range.

The average curves for healthy volunteers with standard deviations (SD) were calculated for wavelengths of excitation at 315 nm, 325 nm and 340 nm and the deviations of the curves from average were in the range of 10% (one SD). To find the differences between serum emission for patients with different metabolic disorders and healthy people, the average normal range (mean and 2 standard deviations) was compared with measurements of serum emission from patients. The following parameters used for the comparison were: the maximum intensity of emission at 470 nm, the maximum intensity of emission at 430 nm, and the ratio of the intensity at 470 nm to the intensity at 430 nm.

Metabolic Disorders

The measurements of the serum emission from patients were grouped in several different sets according to the clinical diagnosis and symptoms: cancer, thyroid disorder, diabetes, arthritis, chronic fatigue syndrome (CFS), cardiovascular disease (CAD), hypertension and fatigue. All of these diseases are associated with different types of metabolic abnormalities. A brief description of the analyses of the serum emission for each of these groups compared to the normal group is presented in Examples 5–8.

EXAMPLE 5

Cancer

Figure 2A:
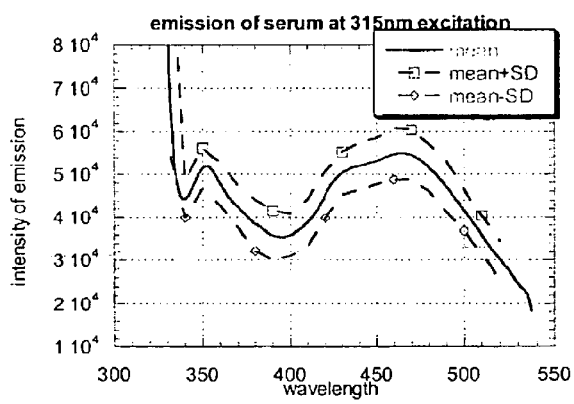
FIG. 2a is the emission of serum at 315 nm excitation for cancer patients as compared to healthy volunteers.
Figure 2:
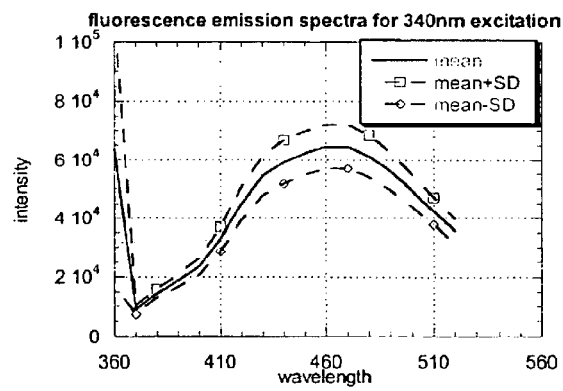
FIG. 2b is the emission of serum at 340 nm excitation.

Data from cancer patients were grouped by types of cancer and the results of the analysis of serum emission are presented in the Figures. For cancer patients, the fluorescence emission curves were different from the normal group and were characterized by a decreased level of serum emission in the 430–500 m range (see in particular FIGS. 2, 4–6 and 13–18). Examples of serum emission for cancer patients (breast cancer, lung cancer, prostate cancer and chronic lymphocytic leukemia) in comparison with the average normal curve are shown on FIGS. 2a and b at 315 nm and 340 nm excitation. A summary of the characteristic parameters of serum emission for patients with different types of cancer (breast cancer, lung cancer, prostate cancer, chronic lymphocytic leukemia and others) is presented in Table 2. The values in the columns describe the following parameters for each patient:

1. the intensity in counts per second of serum emission at 350 nm, 430 nm, and 470 nm (excitation at 315 nm);
2. the percentage difference in the emission intensity of NADH (maximum intensity at 470 nm) for cancer patients in comparison with the average emission intensity at 470 nm for healthy volunteers; and
3. the characteristics of patients and diagnosis.

Figure 4:
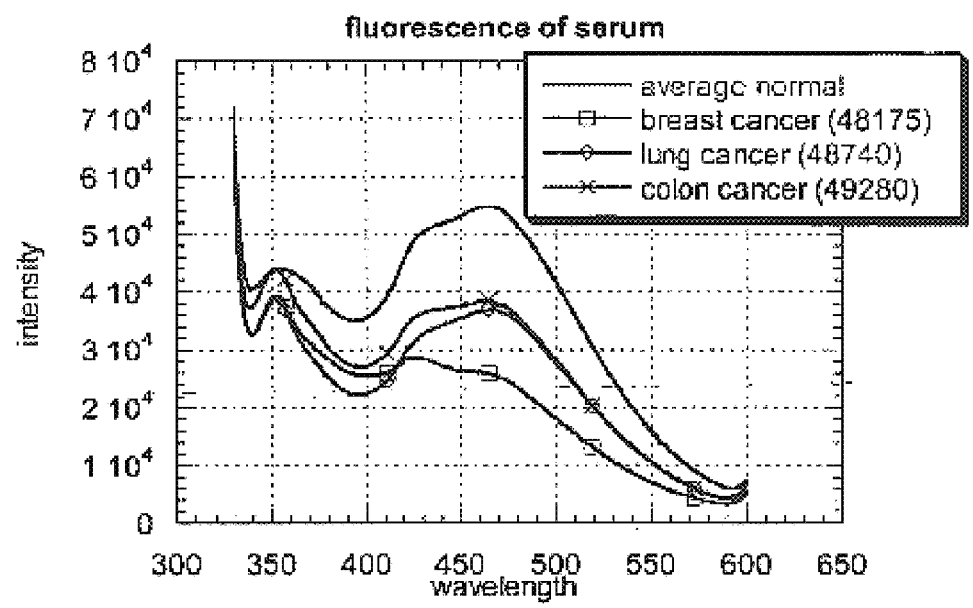
FIG. 4 is the fluorescence of serum among various cancer patients as compared to healthy volunteers.
Figure 5:
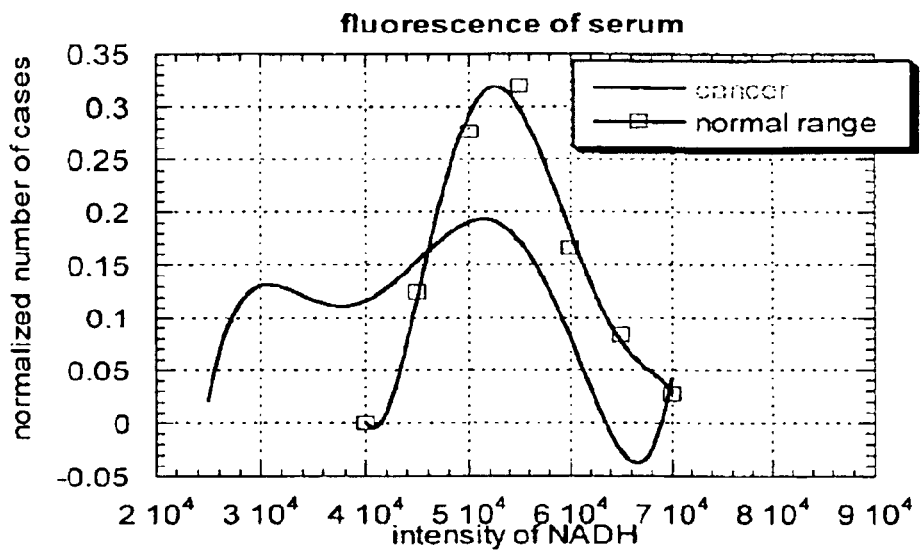
FIG. 5 is the florescence of serum emission intensities at 470 nm for cancer patients as compared to healthy volunteers.
Figure 6:
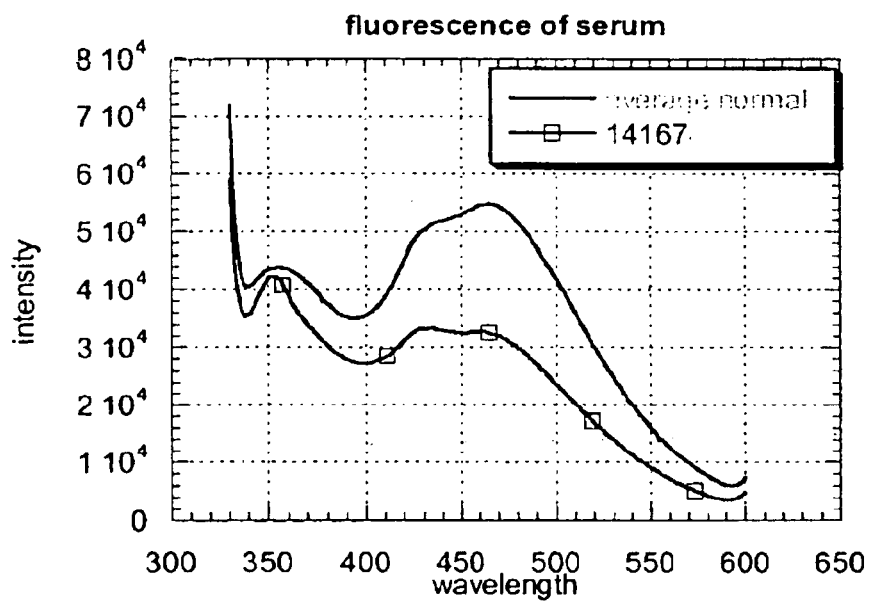
FIG. 6 is the fluorescence of serum of a patient with an ovarian cyst compared to a healthy patient.

The frequency distribution of the measured intensities at 470 nm (fluorescence of NAD(P)H) for healthy volunteers and for patients with cancer was calculated, normalized on the total number of cases and collectively illustrated in FIGS. 4 and 5.

TABLE 1

Extrapolation of frequency curves by the polynomial functions
equation for extrapolation Y = Mo + M1 * x + M2 * x$\hat{\,}$2 + + Mn * X$\hat{\,}$n

|  | Average normal | cancer | diabetes | CAD | Thyroid disorder | fatigue |
|---|---|---|---|---|---|---|
| M0 | −20.996 | −20.996 | 1.8936 | −3.88 | 1.2869 | −2.399 |
| M1 | 0.002536 | 0.0025 | −0.00016 | 0.00045 | −0.000133 | 0.000318 |

TABLE 1-continued

Extrapolation of frequency curves by the polynomial functions
equation for extrapolation $Y = M_0 + M_1 * x + M_2 * x^2 + \ldots + M_n * X^n$

| | Average normal | cancer | diabetes | CAD | Thyroid disorder | fatigue |
|---|---|---|---|---|---|---|
| M2 | −0.001082404 | −0.00108 | 0.000586 | −0.00067 | 0.0005811 | −0.00054 |
| M3 | 1.65894E−05 | 1.66E−05 | 4.61E−06 | 3.45E−06 | −5.5E−06 | 7.19E−06 |
| M4 | 3.57052E−10 | 3.57E−10 | 1.25E−08 | −6.2E−08 | 1.858E−08 | −6.5E−08 |
| M5 | | | | 1.55E−10 | −1.9E−11 | 1.85E−10 |
| coefficient of correlation | 0.99447 | 0.93829 | 0.61897 | 0.9613 | 0.9445 | 0.91192 |

Figure 3:
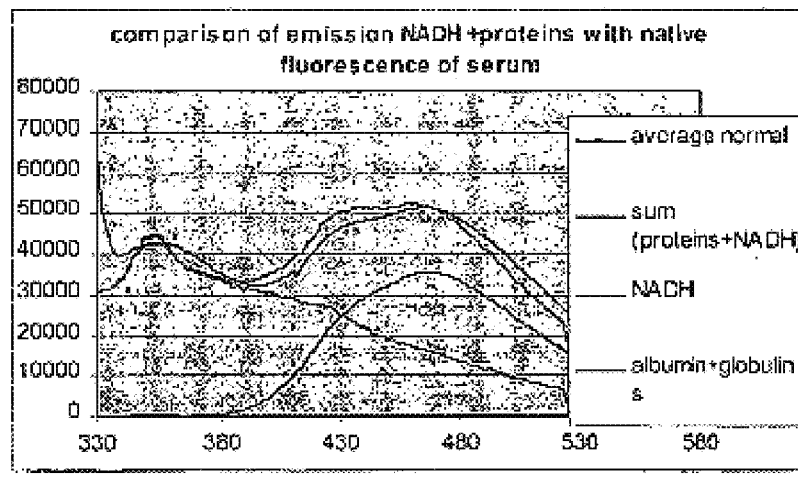
FIG. 3 is a comparison of emission NADH+ proteins with native fluorescence of serum. The numbers are normalized for the total number of cases for healthy volunteers and cancer patients. The frequency distribution of the measured intensities at 470 nm (fluorescence of NAD(P)H) is shown.

The fit for data for these curves was estimated using the Least Square's 4$^{th}$ order polynomial function for data analysis and graphed with Kaleidagraph software. The parameters used to construct the frequency curves fits shown in FIG. 3 are listed in Table 1. The correlation coefficients were 0.99 for serum emission from healthy volunteers and 0.94 for serum emission from cancer patients.

TABLE 2

Level of the serum fluorescence emission for patients with cancer

| Patients (age, sex) | Intensities of serum emission at wavelength | | | Comparison of serum emission changed level of NADH emission at 470 nm (%) | Diagnosis |
|---|---|---|---|---|---|
| | 350 nm | 430 nm | 470 nm | | |
| 38, f | 4.00E+04 | 2.90E+04 | 2.60E+04 | −52.73 | breast cancer |
| 42, f | 3.80E+04 | 3.70E+04 | 3.60E+04 | −34.55 | breast cancer |
| 38, f | 5.00E+04 | 4.40E+04 | 4.90E+04 | −10.91 | breast cancer |
| 45, f | 3.90E+04 | 4.20E+04 | 4.70E+04 | −14.55 | breast cancer |
| 47, f | 4.00E+04 | 4.80E+04 | 4.90E+04 | −10.91 | breast cancer |
| 39, f | 4.80E+04 | 4.80E+04 | 5.40E+04 | −1.82 | breast cancer |
| 77, f | 7.30E+04 | 5.60E+04 | 5.50E+04 | −10.2 | breast cancer, multiple myeloma |
| 80, f | 4.80E+04 | 5.40E+04 | 5.10E+04 | −7.27 | breast cancer, thyroid nodule |
| 80, f | 4.70E+04 | 5.70E+04 | 5.00E+04 | −9.09 | breast cancer |
| 45, f | 5.70E+04 | 4.80E+04 | 4.50E+04 | −18.18 | breast cancer, metastasis |
| 45, f | 4.00E+04 | 4.30E+04 | 4.45E+04 | −19.09 | breast cancer |
| 79, m | 3.00E+04 | 3.90E+04 | 3.50E+04 | −36.36 | chronic lymphocytic leukemia(CLL), |
| 63, f | 4.00E+04 | 3.90E+04 | 4.30E+04 | −21.82 | CLL |
| 73, f | 4.80E+04 | 4.40E+04 | 4.50E+04 | −18.18 | leukemia |
| 60, m | 4.00E+04 | 4.70E+04 | 5.10E+04 | −7.27 | CLL, hypertension |
| | 4.20E+04 | 5.00E+04 | 5.80E+04 | 5.45 | marginal cell leukemia |
| 67, f | 4.30E+04 | 2.90E+04 | 2.70E+04 | −50.91 | lung cancer, metastasis |
| 73, m | 5.20E+04 | 3.70E+04 | 3.90E+04 | −29.09 | lung cancer, arthritis, hypertension |
| 51, m | 3.80E+04 | 3.30E+04 | 3.80E+04 | −30.91 | lung cancer with metastasis |
| 66, m | 3.00E+04 | 3.90E+04 | 3.50E+04 | −36.36 | lung cancer |
| 51, m | 5.80E+04 | 4.60E+04 | 3.80E+04 | −30.91 | lung cancer |
| 36, f | 4.10E+04 | 6.00E+04 | 8.00E+04 | 45.4 | lung cancer with metastasis |
| 53, m | 4.80E+04 | 4.40E+04 | 4.80E+04 | −12.73 | prostate cancer |
| 68, m | 4.30E+04 | 3.90E+04 | 4.40E+04 | −20.0 | prostate cancer |
| 55, m | 5.00E+04 | 4.60E+04 | 4.40E+04 | −20.0 | prostate cancer |
| 69, m | 4.20E+04 | 5.20E+04 | 5.00E+04 | −9.09 | prostate cancer |
| 68, m | 5.00E+04 | 5.50E+04 | 5.80E+04 | 5.45 | prostate cancer |
| 66, m | 4.90E+04 | 5.00E+04 | 5.30E+04 | −3.64 | prostate cancer |
| 69, m | 3.40E+04 | 3.10E+04 | 2.80E+04 | −49.09 | prostate cancer |
| 80, m | 4.20E+04 | 6.30E+04 | 6.80E+04 | 15.0 | prostate cancer |
| 75, m | 4.40E+04 | 3.70E+04 | 3.90E+04 | −29.09 | prostate benign hypertrophy (BPH) |
| 68, m | | 5.50E+04 | 5.40E+04 | −1.82 | cancer prostate |
| 74, m | 5.00E+04 | 5.80E+04 | 5.00E+04 | −9.09 | BPH, abnormal lab test |
| 70, m | 4.80E+04 | 4.20E+04 | 4.00E+04 | −27.27 | cancer prostate |
| 75, m | 4.60E+04 | 5.80E+04 | 6.60E+04 | 20.0 | BPH, fatigue |
| 73, m | 5.90E+04 | 4.00E+04 | 3.50E+04 | −36.36 | cancer prostate |

TABLE 2-continued

Level of the serum fluorescence emission for patients with cancer

| Patients (age, sex) | Intensities of serum emission at wavelength | | | Comparison of serum emission changed level of NADH emission at 470 nm (%) | Diagnosis |
|---|---|---|---|---|---|
| | 350 nm | 430 nm | 470 nm | | |
| 62, m | 4.90E+04 | 4.90E+04 | 5.40E+04 | −1.82 | cancer prostate, hypertension |
| 70, m | 5.20E+04 | | 3.20E+04 | −41.8 | prostatitis, diabetes mellitus |
| 56, m | | 3.70E+04 | 3.90E+04 | −29.09 | benign prostate hypertrophy |
| 74, m | 4.10E+04 | 5.00E+04 | 5.20E+04 | −5.45 | bladder cancer, leukemia, CAD |
| 46, m | 4.80E+04 | 3.20E+04 | 3.00E+04 | −45.45 | hepatitis cancer |
| 57, m | 4.30E+04 | 4.70E+04 | 4.80E+04 | −12.73 | cancer neoplasm |
| 86, m | 4.20E+04 | 4.40E+04 | 4.30E+04 | −21.82 | cancer neoplasm |
| 65, f | 5.80E+04 | 4.70E+04 | 4.80E+04 | −12.73 | ovarian cancer, hypothyroid |
| 54, m | 4.00E+04 | 5.40E+04 | 5.60E+04 | 1.82 | Bladder cancer hypertension |
| 47, f | 4.70E+04 | 3.00E+04 | 3.2E+04 | −41.81 | cancer pancreas |
| 60, m | 4.00E+04 | 4.70E+04 | 5.20E+04 | −5.45 | marginal cell leukemia |
| 39, f | 4.60E+04 | 3.00E+04 | 2.80E+04 | −49.09 | sarcoma |
| 74, f | 4.80E+04 | 2.40E+04 | 2.10E+04 | −61.82 | pancreatic cancer |
| 73, f | 4.40E+04 | 3.70E+04 | 3.80E+04 | −30.91 | colon cancer, hypothyroid |
| 54, f | 4.20E+04 | 3.40E+04 | 3.30E+04 | −40 | ovarian cyst |
| 59, m | 2.80E+04 | 4.80E+04 | 4.75E+04 | −13.64 | multiple myeloma |
| 75, m | 4.20E+04 | 5.50E+04 | 6.00E+04 | 9.09 | malignant lymphoma |
| 51, f | 4.60E+04 | 4.60E+04 | 4.70E+04 | −14.55 | liver cyst, CAD |
| 47, f | 3.60E+04 | 3.40E+04 | 3.50E+04 | −36.36 | ovarian cancer, hypothyroid |
| 47, f | 4.70E+04 | 3.00E+04 | 3.00E+04 | −45.45 | cancer pancreas, arthritis, pain |
| 63, m | | | 3.00E+04 | −45.45 | cancer pancreas, arthritis |
| 75, f | 5.70E+04 | 4.80E+04 | 5.30E+04 | −3.64 | lymphoma malignant, arthritis |
| 70, f | 5.00E+04 | 5.40E+04 | 5.30E+04 | −3.64 | lymphoma malignant, diabetes mellitus |
| 42, f | 5.60E+04 | 4.40E+04 | 4.20E+04 | −23.64 | breast cancer, liver cancer |
| 73, m | | 5.90E+04 | 6.20E+04 | 12.73 | cancer prostate, hypertension, diabetes mellitus |
| 74, f | | 4.80E+04 | 5.00E+04 | −9.09 | leukemia w/o mention of remission |
| 73, m | | 5.90E+04 | 6.20E+04 | 12.7 | cancer prostate, diabetes mellitus |

BPH = benign prostatic hypertrophy,
CFS = chronic fatigue syndrome,
CAD = cardiovascular disease,
MC leukemia = marginal cell leukemia The distribution of frequencies in FIG. 5 for the cancer study was found to be bimodal. Two peaks were found, one at $3.0\times10^4$ and the other at $5.1\times10^4$. For the cases evaluated, breast cancer, lung cancer and leukemia tended to fall into the lower intensity domain whereas prostate cancer gave higher intensity values.

The sensitivity of the method for cancer was defined as the percentage of patients with disease whose level of serum emission fell below the reference value (RV), which was chosen as the point of intersection of frequency distribution of emission with the normal distribution curve. The percentage of patients with a level of emission less than the reference value was 48% of all patients with cancer. The percentage of patients with different types of cancer whose level of fluorescence serum emission was below the average normal emission was also calculated. The data indicated that 80% of patients with lung cancer, 75% of patients with chronic lymphatic leukemia, 75% of patients with bladder, ovarian, colon and pancreatic cancer, and 64% of the patients with breast had more than a 10% decrease in the level of serum emission intensity at 470 nm. Only serum from 54% of the cases with prostate cancer underwent a decrease in emission intensity.

The data was also evaluated for the ratio of the emission intensity at 430 nm compared to emission intensity at 470 nm. For healthy volunteers, $I_{430}/I_{470}$ was $0.92\pm0.04$; for cancer patients $I_{430}/I_{470}$ was $1.01\pm0.09$. The statistical significance between mean values was reached at p-value less than 0.001.

Figure 12:
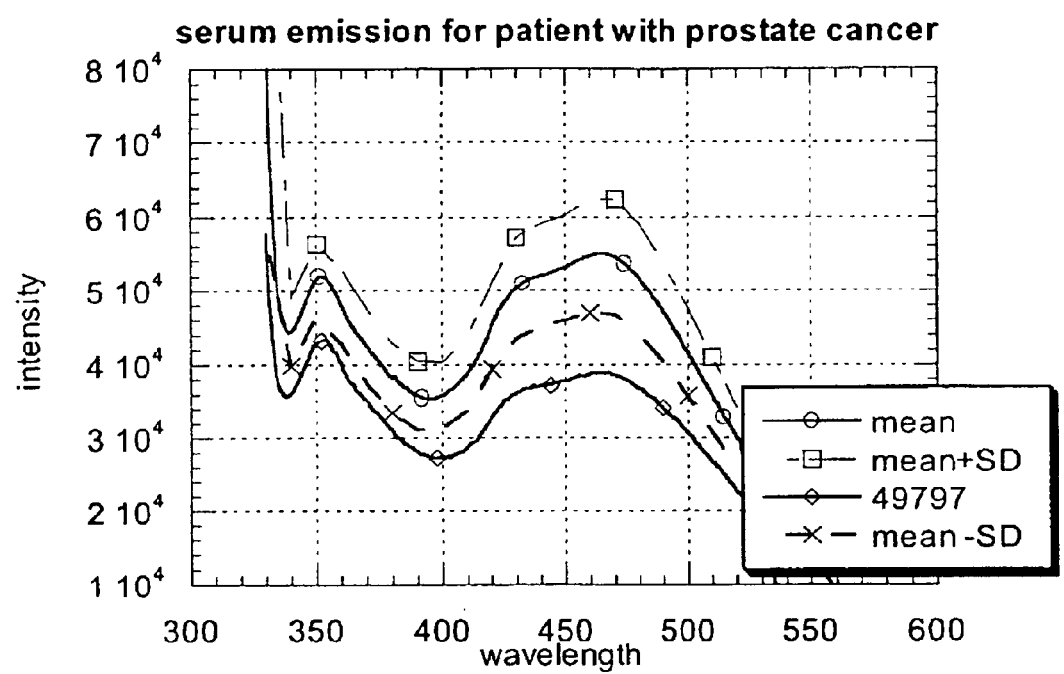
FIG. 12 is the distribution of serum emission at 470 nm for a patient with prostate cancer as compared to the mean normal +/−1 standard deviation.
Figure 13:
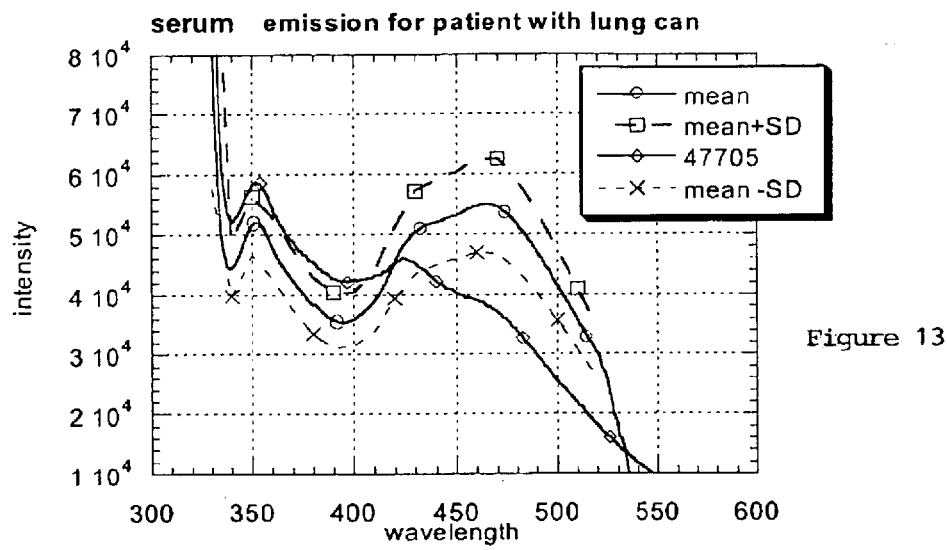
FIG. 13 is the distribution of serum emission for a patient with lung cancer as compared to the mean normal +/−1 standard deviation.
Figure 14:
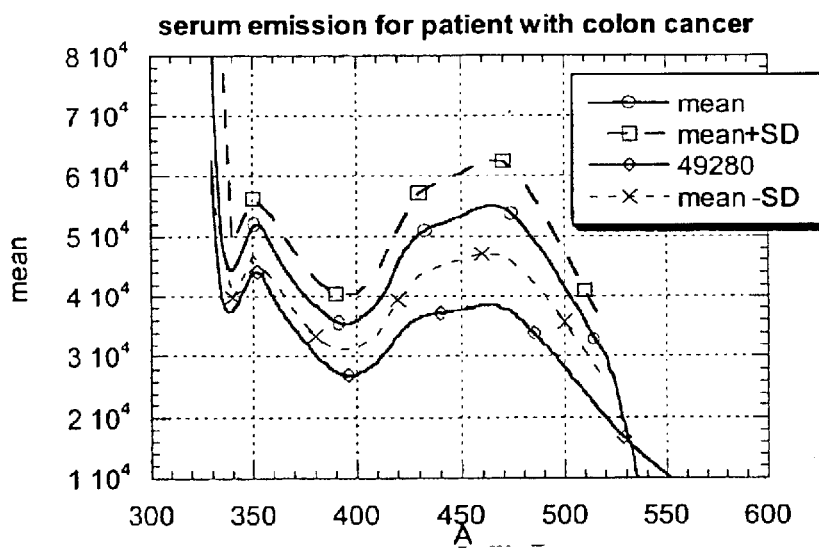
FIG. 14 is the distribution of serum emission for a patient with colon cancer as compared to the mean normal +/−1 standard deviation.
Figure 15:
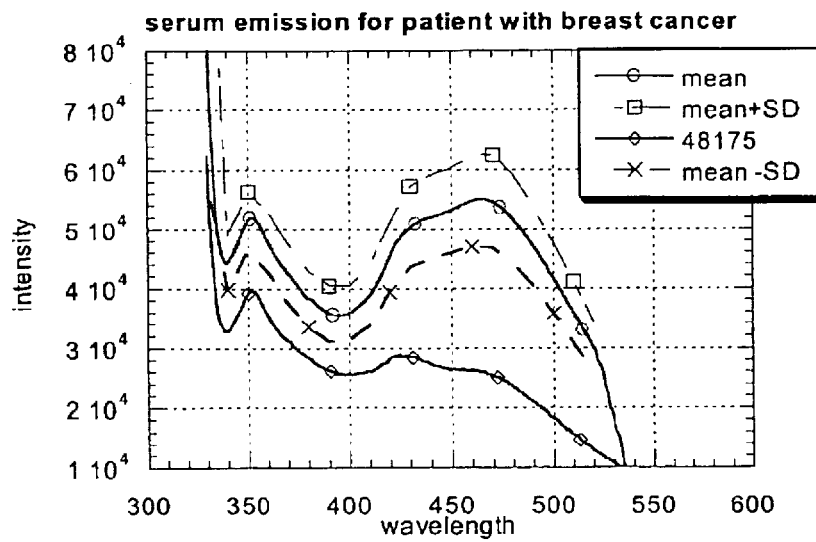
FIG. 15 is the distribution of serum emission for a patient with breast cancer as compared to the mean normal +/−1 standard deviation.
Figure 16:
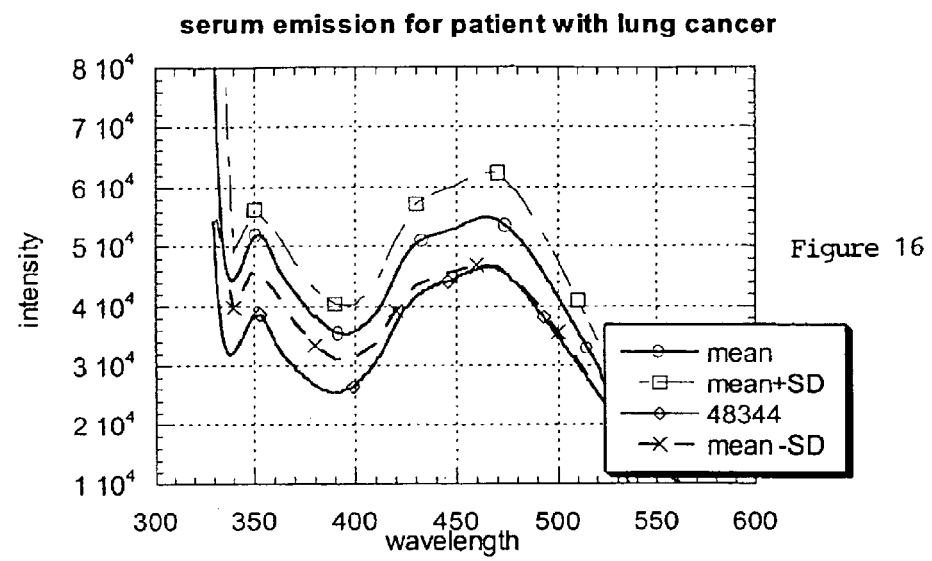
FIG. 16 is the distribution of serum emission for a patient with breast cancer as compared to the mean normal +/−1 standard deviation.
Figure 17:
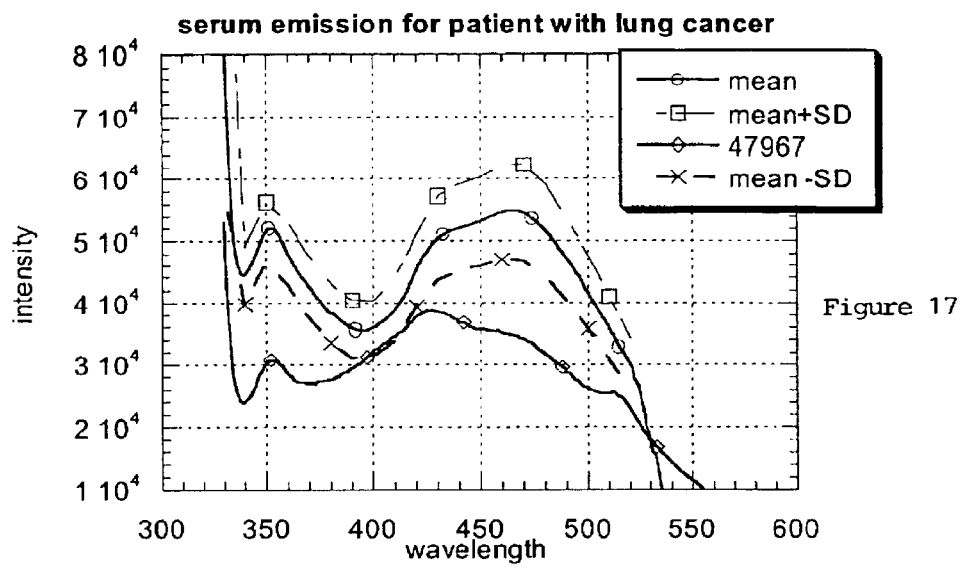
FIG. 17 is the distribution of serum emission for a patient with lung cancer as compared to the mean normal +/−1 standard deviation.
Figure 18:
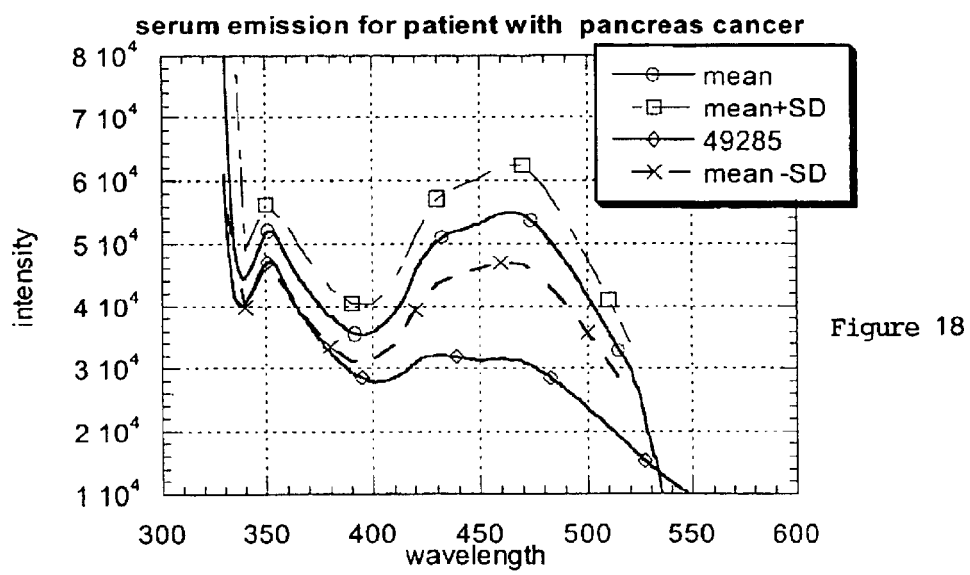
FIG. 18 is the distribution of serum emission for a patient with pancreas cancer as compared to the mean normal +/−1 standard deviation.
Figure 19:
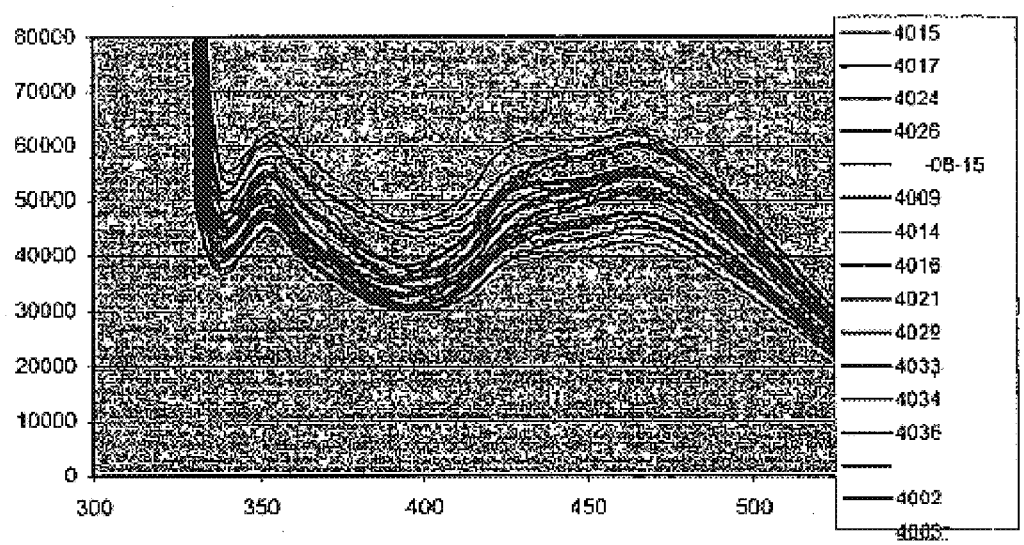
FIG. 19 is a distribution of serum emission for 14 normal patients.
Figure 20:
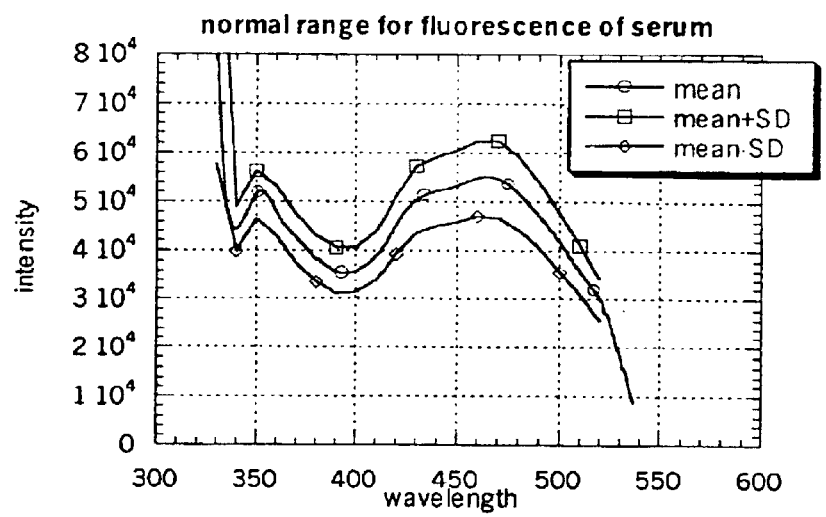
FIG. 20 is a distribution of serum emission at 470 nm for normal patients showing +/− standard deviation.
Figure 21:
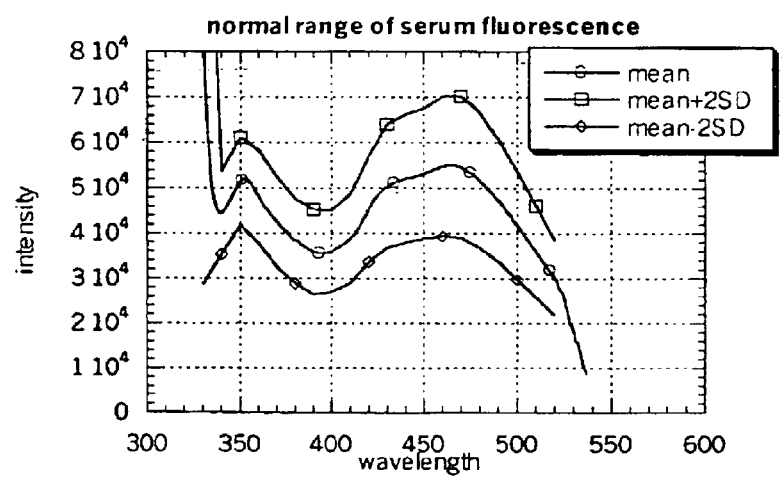
FIG. 21 is a distribution of serum emission at 470 nm for normal patients showing +/−2 standard deviations.
Figure 22:
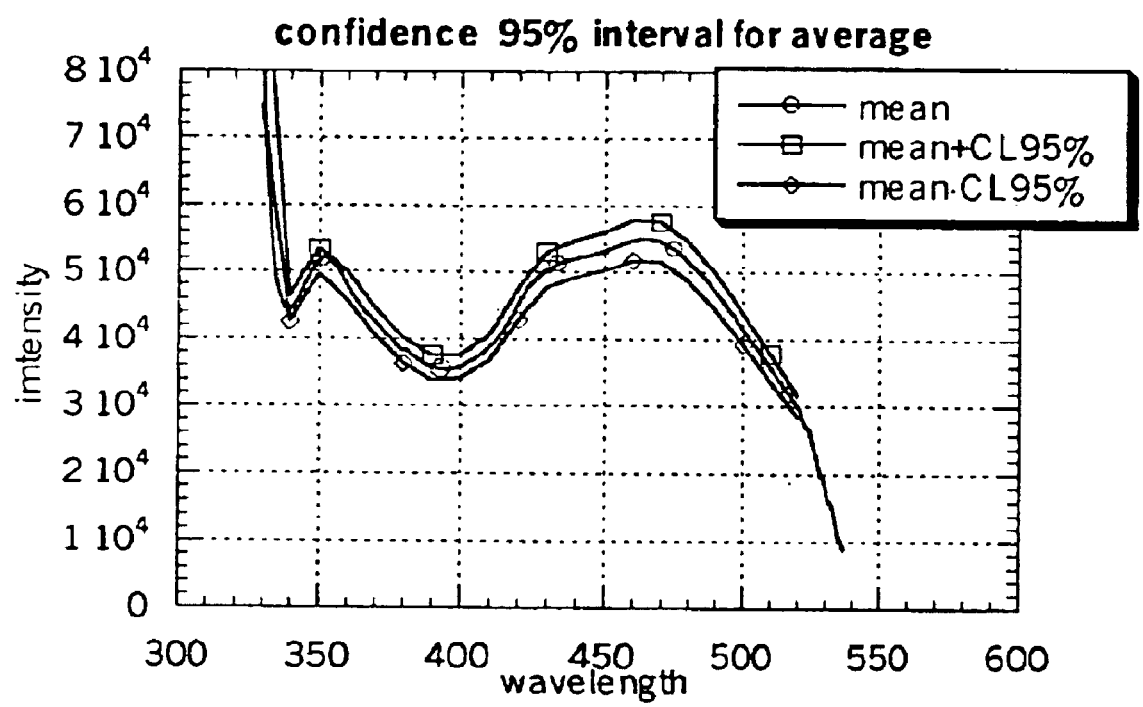
FIG. 22 is a distribution of serum emission for normal patients showing 95% interval from average.
Figure 23:
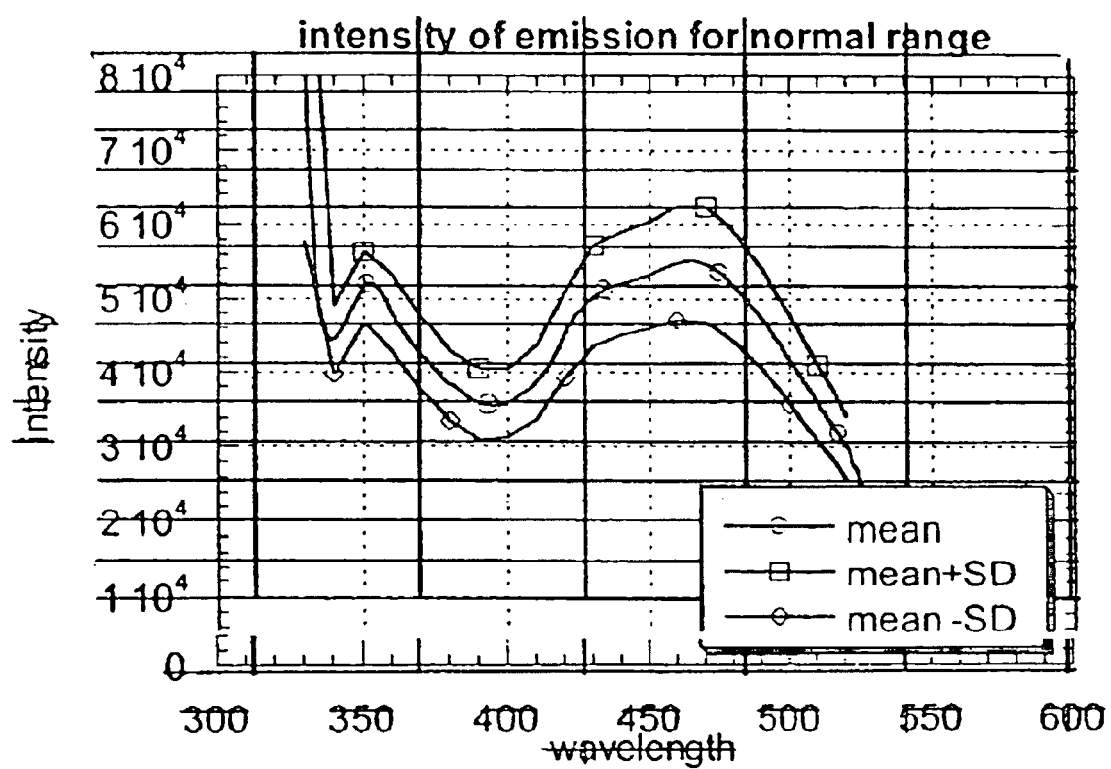
FIG. 23 is a distribution of serum emission at 470 nm for normal patients showing +/− standard deviation.

Serum fluorescence intensity at 470 nm (NAD(P)H emission) was lower for cancer patients than the intensity of emission at the same wavelength for the normal range. The fluorescence intensity for various cancer patients can be seen the following figures: a prostate patient can be seen in FIG. 12, lung cancer can be seen in FIGS. 13 and 17, colon can be seen in FIG. 14, and breast cancer can be seen in FIGS.

15 and 16. Without being restricted to the following explanation, this observation may indicate an increased energy demand of cells and a corresponding decrease in the concentration of NADH in cells and serum. In many types of tumor cells the interlocking coordination may be defective. Glycolysis, pyruvate oxidation, the citric acid cycle and oxidative phosphorylation are regulated by the relative concentrations of ATP, ADP and NADH and the changed metabolic rate may influence the concentration of these molecules. Also at least some cancer cells undergo a decrease in T3 receptors, a decrease in response to T3 receptors and a decrease in production of T3 and T4 receptors. Additional evidence that cancer patients may have below normal levels of serum NADH comes from the fluorescence spectroscopy measurements of virus-transformed cells. The significant difference between normal and transformed cells appeared to involve intracellular NADH metabolism, which results in a much lower fraction of free NADH.

In addition, the concentration of adenine (ATP, ADP, AMP) and pyridine (NAD(P), NAD(P)H) nucleotides in the erythrocytes may be changed for patients with cancer. Possibly, if the level of ATP is lower in the erythrocytes of the subjects affected by tumors, it also may be accompanied by modifications in the concentrations of other energetic molecules and result in a lower level of NAD(P) in cells as well as a lower level of coenzymes in serum.

As the main fraction of NAD(P)H in serum is due to leakage from cells, all these observed effects may be the reason for a decreased level of serum emission at 470 nm.

The changed ratio of emission ($I_{430}/I_{470}$) for cancer patients in comparison with healthy volunteers may be explained in one of two ways. NAD(P)H has a different fluorescence emission maximum in the free form (460 nm) and enzyme-bound form (440 nm), the difference in intensities of these two maxima possibly may account for the difference in concentration of serum bound and free NADH for cancer patients and healthy volunteers. Another possibility may be that the emission intensity of the pyridoxal-5-phosphate (PLP), which has its emission maximum at 430 nm, contributes more significantly to the total emission spectrum of serum according to decreased emission at 470 nm.

In example 6, the same analysis is performed for hypothyroidism and hyperthyroidism.

EXAMPLE 6

Hypothyroidism and Hyperthyroidism

Figure 7:
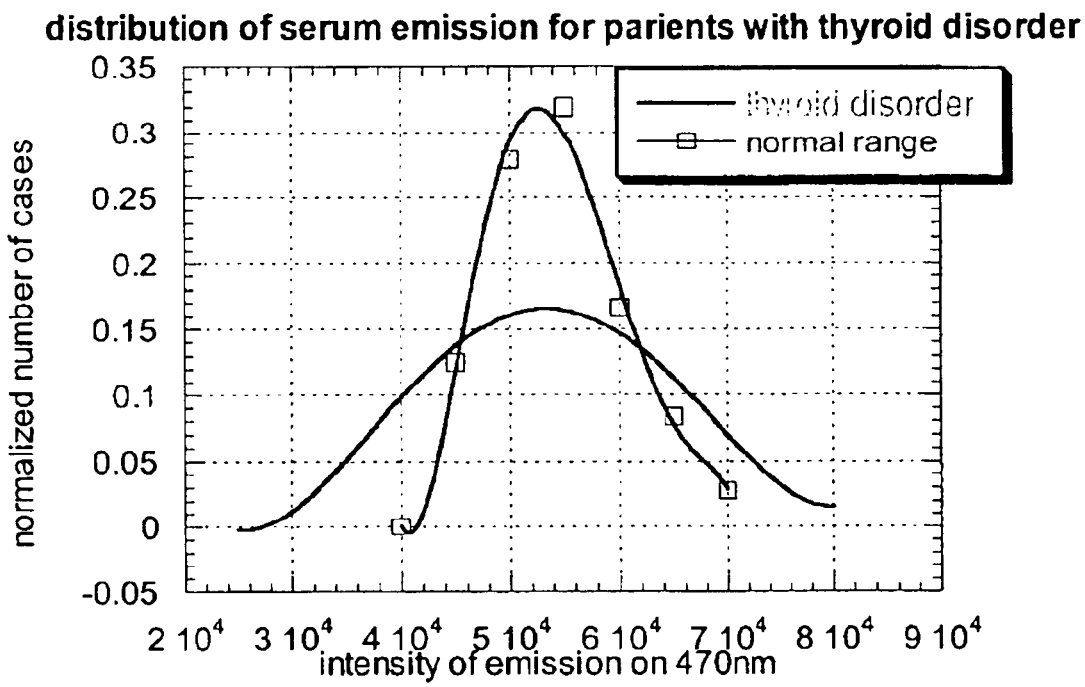
FIG. 7 is the distribution of serum emission intensities at 470 nm for patients with thyroid disorder as compared to healthy volunteers.

Hypothyroidism and hyperthyroidism cause large changes in metabolism. For patients with thyroid disorders, the disease causes lowered basal metabolism (hypothyroidism) or increased basal metabolism (hyperthyroidism). The set of data, which was analyzed for these kinds of diseases, included 53 patients: 4 patients with hyperthyroidism, 11 patients with an unspecified thyroid disorder and all others with hypothyroidism. The distribution of maximum emissia at 470 nm for all patients with thyroid disorders is shown in FIG. 7. The distribution of measured intensities of serum emission for this group of patients was evaluated by the polynomial function referred to earlier, resulting in a correlation coefficient of 0.94 (Table 1). The result indicated that the distribution of serum emission was different from the normal distribution and was mostly decreased for patients with hypothyroidism (31% of patients had a level of emission 20% lower than the average normal, but 8% had an increase) and increased for patients with hyperthyroidism. The percentage of patients with an emission less intense than the reference value was 56% for patients with hypothyroidism and the percentage of patients with a level of emission greater than the reference was 50% for those with hyperthyroidism.

The ratio of intensities of emission at 430 nm to 460 nm was in the range of 1.018±0.11 for patients with hypothyroidism and showed a significant difference compared to the average ratio for healthy volunteers at the level $p<0.05$ (t-test for means with unequal variances).

For all patients with this kind of metabolic disorder, the alterations were also observed in blood thyroid hormones. A direct correlation between abnormalities of hormone secretion, for example, the level of TSH (thyroid stimulating hormone), with the level of fluorescence emission at 470 nm was found. The level of TSH was high for samples giving rise to a lower level of serum fluorescence emission and low for the samples giving rise to higher levels of serum emission.

For patients with hypothyroidism and hyperthyroidism the relationship between thyroid hormone and metabolism is well documented, which also may affect the level of NADH. Hypo- and hyperthyroidism results in lower and higher contents of thyroid hormone, which may play a role in regulation of the synthesis of NAD(P) from tryptophan and changed levels of coenzymes in serum. The hyperthyroid state led to an increase in work rate and resulted in an increase in the oxidation-reduction turnover number, which also may change the concentration of cytosolic NADH. For hypothyroidism, a decreased level of enzymatic activity, metabolic rate and a decline in the level of hormones may cause a lower content of NAD(P)H in cells and in serum.

In Example 7 the same analysis was performed on patients with disorders in carbohydrate metabolism.

EXAMPLE 7

Diabetes

For patients with disorders in carbohydrate metabolism resulting in changed blood glucose concentrations, analysis of serum samples also showed altered levels of emission in the visible range which was compared with the level of blood glucose and fructosamine in Table 3. The normal range for blood glucose is 65–125 mg/dl and normal range for fructosamine is 175–272 microM/l. Comparison between the intensity of emission at 470 nm and the concentration of fructosamine in blood showed a strong correlation (with a correlation coefficient of 0.6) and a weaker correlation was seen with the glucose level.

For diabetic patients the changes in the glucose/glycogen metabolism and the failure to metabolize ingested carbohydrate or the overproduction of glucose has an effect on levels of NADH and, thus, emission of serum at 470 nm. Diabetes is accompanied by the development of hyperglycemia and an increase in the rate of hemoglobin and albumin glycosylation. Hyperglycemia may also result in an imbalance in cytosolic NADH/NAD+ and possibly an increased level of NADH, as nicotinamide adenine dinucleotide and its derivatives have regulatory functions in glucose metabolism and the generation of pyruvate from glucose.

TABLE 3

Disorder in Carbohydrate Metabolism

| Patient Age, sex | intensity at 350 nm | intensity at 430 nm | intensity at 470 nm | Δ* NADH | glucose** | Fructosamine*** | Disorder |
|---|---|---|---|---|---|---|---|
| 51, f | 5.00E+04 | 6.00E+04 | 6.70E+04 | 21.82 | 91 | | Diabetes, thyroid dis. |
| 61, m | 4.40E+04 | 4.70E+04 | 4.90E+04 | −10.91 | 128 | 282 | Hyperglyc., hypertension |
| 69, m | 5.00E+04 | 5.20E+04 | 5.20E+04 | −5.45 | 212 | 391 | Diabetes, hyperlipidemia, HBP |
| 54, m | 5.10E+04 | 6.80E+04 | 6.80E+04 | 23.64 | 154 | | Diabetes, CFS, hyperlipid., hypertension |
| 50, f | | | 5.40E+04 | −1.82 | 149 | | Diabetes, CAD |
| 54, f | 5.00E+04 | 5.50E+04 | 6.50E+04 | 18.18 | | 249 | Diabetes |
| 67, m | 4.70E+04 | 5.00E+04 | 5.50E+04 | 0 | 169 | | Diabetes, CFS |
| 51, f | 4.20E+04 | 6.00E+04 | 6.80E+04 | 23.64 | | | hypoglycemia |
| 67, m | 5.00E+04 | 5.00E+04 | 5.50E+04 | 0 | 159 | | Allergy, Diabetes, CFS |
| 63, f | 3.40E+04 | 5.40E+04 | 5.60E+04 | 1.82 | 88 | | Gastritis, hypoglycemia, |
| 48, f | 4.60E+04 | 6.20E+04 | 5.80E+04 | 5.45 | 128 | | Diabetes type 1, hyperthyroid |
| 53, m | | 6.20E+04 | 6.90E+04 | 25.45 | 179 | 316 | ASHD, hypertension, diabetes |
| 58, m | 4.70E+04 | 7.30E+04 | 7.80E+04 | 41.82 | 238 | 650 | Diabetes-mellitus, hyperlipidemia |
| 58, m | 5.20E+04 | 8.10E+04 | 7.90E+04 | 43.64 | | | Diabetes, hyperlipidemia |
| 50, f | 5.00E+04 | 5.70E+04 | 6.70E+04 | 21.82 | 90 | | Diabetes, thyroid dis. |
| 60, m | 4.70E+04 | 6.40E+04 | 7.60E+04 | 38.18 | 235 | 550 | diabetes |

Figure 9:
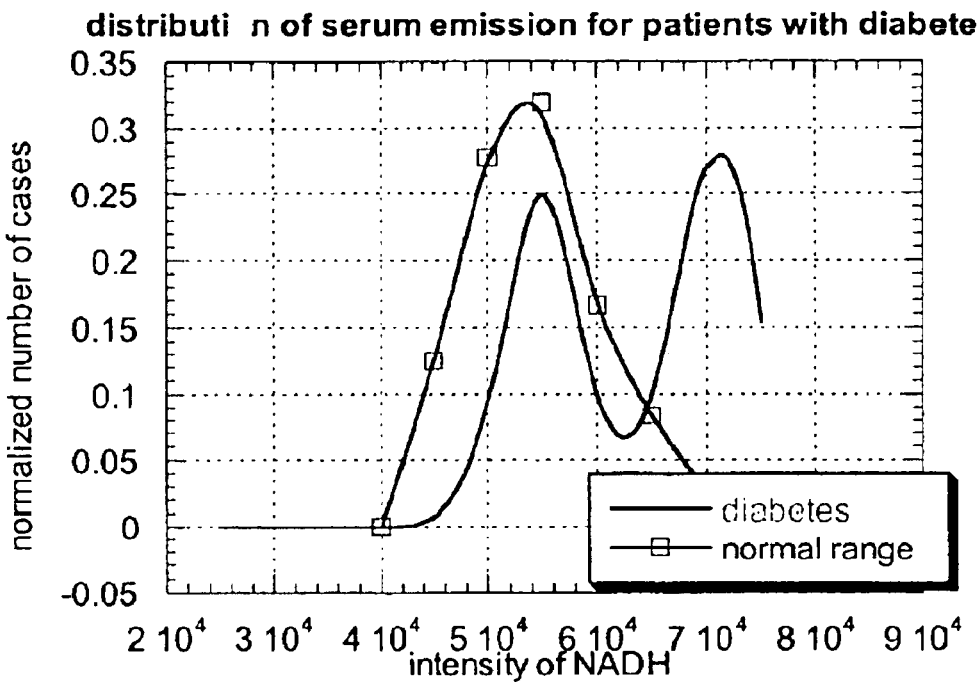
FIG. 9 is the distribution of serum emission at 470 nm for patients with diabetes as compared to healthy volunteers.

*changed
**normal range 65–125
***normal range 175–272,
ASHD = atherosclerotic heart disease When the distribution of serum emission for patients with diabetes mellitus was compared with serum emission from healthy volunteers in FIG. 9, the distribution for the cases examined was bimodal. At either maximum, the emission intensity was greater than for healthy volunteers. For this group of patients, also, the ratio of serum emission intensities at 430 nm and 470 nm was lower than normal range and equaled 0.809±0.05, which indicated on increased level of serum emission at 470 nm.

In Example 8, the serum emissions from patients with fatigue and arthritidies is measured.

EXAMPLE 8

Fatigue and Arthritidies

Figure 10:
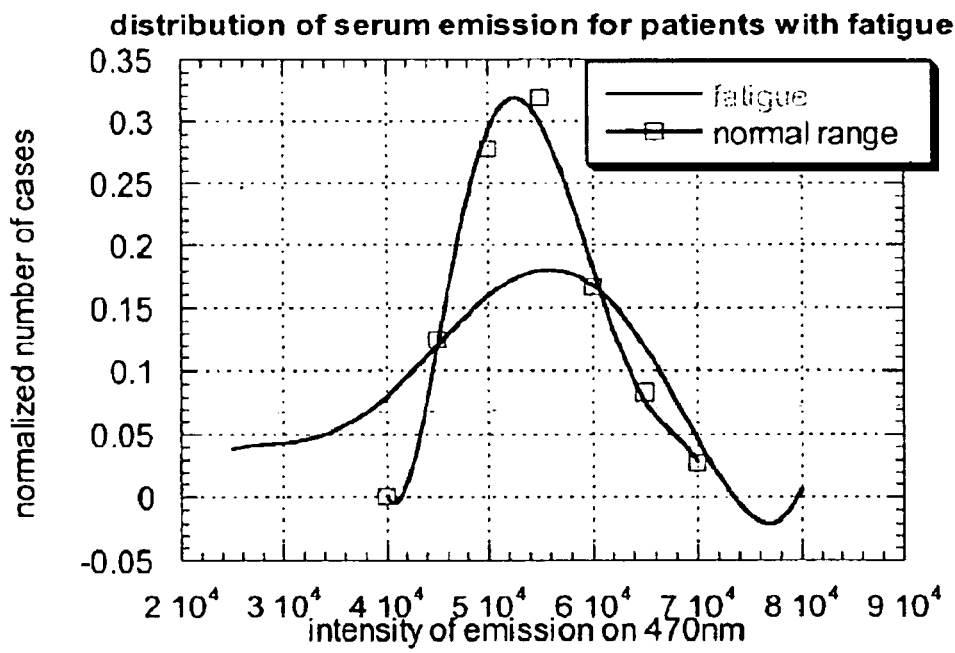
FIG. 10 is the distribution of serum emission at 470 nm for patients with fatigue as compared to healthy volunteers.

Serum emissions from patients with fibromyalgia and symptoms of fatigue were examined and the results are tabulated in Table 4. The frequency distribution of emission for this group of patients is shown in FIG. 10. The emission curves for patients with chronic fatigue and fibromyalgia syndromes showed decreased levels of emission in the visible range in 60% of analyzed cases.

The patients with chronic fatigue syndrome and fibromyalgia showed decreased levels of metabolism according to deficiencies of carbohydrates, proteins, minerals or vitamins, probably because these disturbances interfere with the supply of oxygen to tissues, infectious diseases and many other conditions. Also the fatigue and fibromyalgia syndromes may have a metabolism-dependant character and may result from inadequate thyroid hormone regulation. There are indications that in many cases fibromyalgia is caused by inadequate thyroid hormone regulation of cell function. This results from one of two phenomena: thyroid hormone deficiency or partial resistance of cells to thyroid hormone. All of these conditions may alter body metabolism and change the rate of reactions and the relative concentrations of enzymes and coenzymes. For patients with fatigue the measurements showed a changed level of metabolism and a lower level of serum emission. This was confirmed by previous results, which showed that NADH may be a valuable adjunctive therapy in the treatment of chronic fatigue syndrome.

For patients with arthritis the level of emission showed higher values and lower values than normal, which possibly also indicates a changed redox in cells or a disturbance of tryptophan metabolism. The increased or decreased level of energy metabolism may depend on the level of inflammatory disease of patients or possibly on the level of activation of neutrophils and lymphocytes.

TABLE 4

Serum emissions from patients with fibromyalgia and symptoms of fatigue

| Patient age, sex | 350 nm | 430 nm | 470 nm | % of decreased | disorder |
|---|---|---|---|---|---|
| 24, f | 4.50E+04 | 3.90E+04 | 3.90E+04 | −29.09 | fatigue |
| 43, f | 4.20E+04 | 4.80E+04 | 4.80E+04 | −12.73 | Fibromyalgia, CFS, osteoporosis, arthritis |
| 41, f | 4.70E+04 | 4.00E+04 | 3.80E+04 | −30.91 | fatigue |
| 44, f | 4.90E+04 | 7.10E+04 | 7.50E+04 | 36.36 | Fibromyalgia, edema, CFS |

TABLE 4-continued

Serum emissions from patients with fibromyalgia and symptoms of fatigue

| Patient age, sex | 350 nm | 430 nm | 470 nm | % of decreased | disorder |
|---|---|---|---|---|---|
| 60, f | 4.20E+04 | 4.60E+04 | 4.80E+04 | −12.73 | fatigue |
| 25, m | 4.40E+04 | 4.80E+04 | 5.30E+04 | −3.64 | Allergy, CFS |
|  | 4.30E+04 | 5.40E+04 | 5.50E+04 | 0 | CFS, CAD |
| 31, f | 5.10E+04 | 5.10E+04 | 5.00E+04 | −9.09 | fibromyalgia |
| 72, f | 5.00E+04 | 5.00E+04 | 5.80E+04 | 5.45 | CFS, fibromyalgia |
| 27, f | 4.20E+04 | 5.60E+04 | 5.20E+04 | −5.45 | Fatigue, psoriasis |
| 46, f | 4.70E+04 | 4.70E+04 | 5.00E+04 | −9.09 | CFS |
| 60, m | 4.20E+04 | 5.90E+04 | 6.10E+04 | 10.91 | fatigue |
| 25, f | 3.80E+04 | 2.60E+04 | 2.50E+04 | −54.55 | fatigue |
|  | 4.60E+04 | 4.80E+04 | 5.50E+04 | 0 | CFS, fibromyalgia, joints |
| 72, m | 4.30E+04 | 5.60E+04 | 6.60E+04 | 20 | fatigue |
| 34, f | 5.50E+04 | 4.10E+04 | 4.60E+04 | −16.36 | CFS, candidiosis, pain, fatigue |
|  | 5.00E+04 | 5.00E+04 | 5.50E+04 | 0 | Malnutrition, diabetes, CFS |
| 80, f | 5.00E+04 | 5.50E+04 | 4.70E+04 | −14.55 | Fatigue, candida |
| 65, f | 4.40E+04 | 4.20E+04 | 3.70E+04 | −32.73 | fatigue |
| 38, f | 4.10E+04 | 3.40E+04 | 3.70E+04 | −32.73 | Gastritis, fatigue |
|  | 3.40E+04 | 5.30E+04 | 5.60E+04 | 1.82 | Myositis/myalgia, fibromylagia, gastritis |
| 69, m | 4.40E+04 | 5.60E+04 | 5.60E+04 | 1.82 | fatigue |
| 39, f | 4.40E+04 | 3.10E+04 | 3.20E+04 | −41.82 | Post-traumatic pain, fibromyalg. |
| 16, m | 4.30E+04 | 5.00E+04 | 5.40E+04 | −1.82 | Fatigue, depression |
| 16, f | 4.90E+04 | 3.00E+04 | 2.90E+04 | −47.27 | CFS, arthritis |
| 54, f | 4.70E+04 | 6.00E+04 | 6.00E+04 | 9.09 | Fatigue, myositis |
| 19, m | 5.60E+04 | 5.60E+04 | 6.50E+04 | 18.18 | CFS, depression |
| 23, f | 5.00E+04 | 4.50E+04 | 4.50E+04 | −18.18 | Depression, tendonitis |
| 34, f | 5.00E+04 | 4.00E+04 | 4.40E+04 | −20 | Bipolar, headaches, memory loss |
| 32, f | 5.90E+04 | 5.00E+04 | 5.40E+04 | −1.82 | CFS, sinusitis |
| 53, f | 5.70E+04 | 5.50E+04 | 5.80E+04 | 5.45 | CFS, myositis, tendonitis |
| 42, f | 4.60E+04 | 3.90E+04 | 3.80E+04 | −30.91 | myositis |
| 16, f | 5.00E+04 | 3.00E+04 | 2.90E+04 | −47.27 | CFS, arthritis |
| 34, f | 5.50E+04 | 4.20E+04 | 4.60E+04 | −16.36 | CFS, candidiosis, pain, depression, fatigue |
| 23, f | 5.00E+04 | 4.50E+04 | 4.40E+04 | −20 | Candidiasis, depression, tendonitis |
| 19, m | 5.60E+04 | 5.60E+04 | 6.50E+04 | 18.18 | CFS, depression |
| 54, f | 5.60E+04 | 6.00E+04 | 6.00E+04 | 9.09 | Fatigue, myositis |
| 59, f | 6.80E+04 | 6.70E+04 | 7.00E+04 | 27.27 | Fatigue, myositis |
|  |  | 4.50E+04 | 5.40E+04 | −1.82 | Fatigue, sinusitis |
|  |  | 6.20E+04 | 6.00E+04 | 9.09 | fatigue |

CFS = chronic fatigue syndrome,
CAD = coronary artery disease

In Example 9, the serum emissions from patients with coronary disease is measured.

EXAMPLE 9

Coronary Disease

Figure 8:
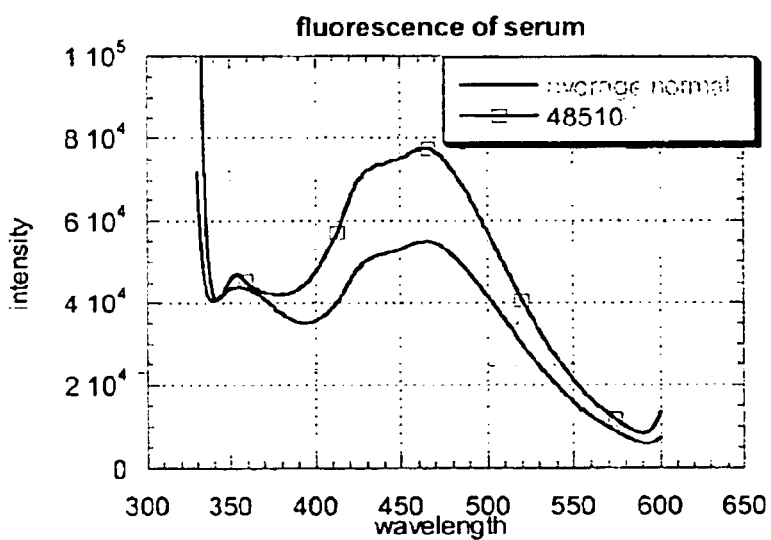
FIG. 8 is the fluorescence of serum for a patient with hypertension as compared to healthy volunteers.
Figure 11:
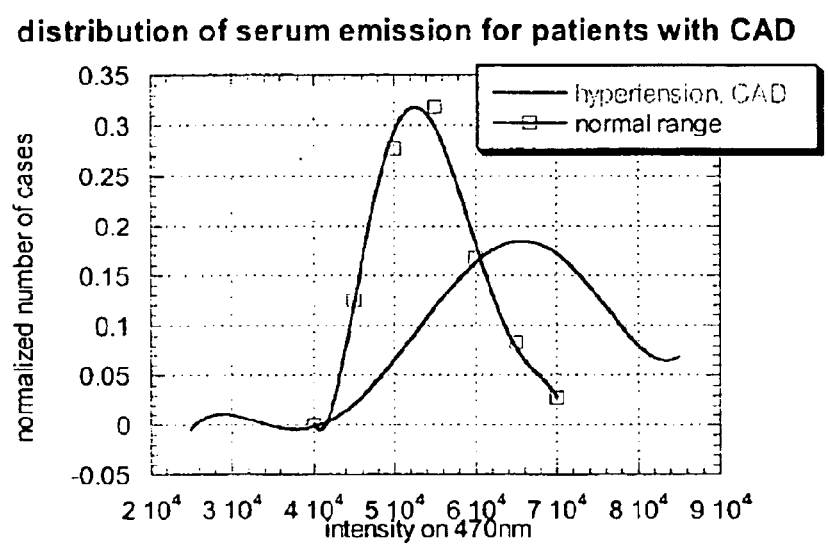
FIG. 11 is the distribution of serum emission for patients with CAD as compared to healthy volunteers.

Table 5 contains data of serum emission from 8 patients with coronary artery disease (CAD) and 17 samples from patients with hypertension (see FIG. 8 also). The serum emission intensity for the patients with coronary artery disease was higher than the normal range. The frequency distribution of serum emission at 470 nm for this group of patients is shown in FIG. 11. The majority of cases gave rise to greater emission intensity than for healthy volunteers.

For patients with hypertension and coronary artery disease the level of serum emission was higher than normal. This may be because the development of hypertension may cause an increase in enzymatic activity involved in oxidative metabolism, an elevated level of glycolytic activity, and NAD/NADH overactivity and a shift to a more reduced or more oxidized form. According to the data for hypertension conditions and CAD, the NAD/NADH state was shifted to a more reduced form. In addition, past research has shown that oral supplementation by this agent had the potential to lower blood pressure and benefited the cardiovascular system as did supplementation with coenzyme Q10.

TABLE 5

Serum emission for patients with coronary artery disease (CAD)

| Patients Age, sex | int350 | 430 | 470 | % of dif. | diagnosis |
|---|---|---|---|---|---|
| 71, m | 4.80E+04 | 6.05E+04 | 6.10E+04 | 10.90909 | coronary artery disease |
| 74, m | 5.30E+04 | 5.90E+04 | 6.50E+04 | 18.18182 | coronary artery disease |

TABLE 5-continued

Serum emission for patients with coronary artery disease (CAD)

| Patients Age, sex | int350 | 430 | 470 | % of dif. | diagnosis |
|---|---|---|---|---|---|
| 67, m | 4.60E+04 | 7.00E+04 | 6.00E+04 | 9.090909 | coronary artery disease |
| 51, m | 4.80E+04 | 7.50E+04 | 7.90E+04 | 43.63636 | CAD, hyperlipidemia |
| 74, m | 4.70E+04 | 6.50E+04 | 6.20E+04 | 12.72727 | CAD |
| 56, m | 4.00E+04 | 80000 | 7.40E+04 | 34.54545 | CAD, hypertension, allergy |
| 83, m | 4.90E+04 | 7.00E+04 | 7.20E+04 | 30.90909 | ischemic heart disease |
| 86, m | 7.40E+04 | 7.50E+04 | 7.70E+04 | 40 | ASHD, arthritis |
| 63, m | | 4.40E+04 | 4.50E+04 | −18.18 | CAD |
| 73, m | 5.40E+04 | 5.90E+04 | 6.00E+04 | 9.090909 | hypertension, fatigue |
| 63, f | 4.90E+04 | 6.00E+04 | 5.80E+04 | 5.454545 | hypertension, hyperlipidemia, thyroid disorder (unspecified) |
| 44, f | 5.60E+04 | 4.80E+04 | 5.50E+04 | 0 | hypertension, hypothyroidism, depression, overweight |
| 45, f | 5.40E+04 | 5.70E+04 | 6.50E+04 | 18.18182 | CFS, hepertension, cytomegalic virus |
| 66, m | 5.30E+04 | 6.20E+04 | 6.50E+04 | 18.18 | arthritis, hypertension |
| 62, f | 4.40E+04 | 5.90E+04 | 6.10E+04 | 10.91 | hypertension, fatigue |
| 72, f | 4.50E+04 | 6.20E+04 | 6.90E+04 | 25.45 | hypertension, arthritis |
| 63, m | 4.70E+04 | 4.20E+04 | 4.70E+04 | −14.55 | arrhythmia, |
| 60, m | 4.70E+04 | 5.60E+04 | 6.80E+04 | 23.64 | arrhythmia, hyperlipidemia |
| 76, f | 5.20E+04 | 6.40E+04 | 7.40E+04 | 34.55 | arthritis, hypertension, CFS, peripheral neuropathy, tendonitis |
| 77, f | 5.60E+04 | 7.60E+04 | 9.50E+04 | 72.73 | hypertension, arthritis, CFS, hyperlipidemia. |
| 54, f | 5.00E+04 | 5.10E+04 | 5.80E+04 | 5.45 | hypertension, hypolipidemia, arthritis |
| 69, m | 5.50E+04 | 7.50E+04 | 8.30E+04 | 50.91 | hypertension, cancer prostate, hyperlipidemia |
| 61, f | 5.00E+04 | 5.60E+04 | 6.00E+04 | 9.09 | inflammatory disorder, arthritis, the cardiac abnormalities |
| 69, m | 5.50E+04 | 5.40E+04 | 5.20E+04 | −5.45 | coronary artery disease |
| 44, f | 5.40E+04 | 5.80E+04 | 6.60E+04 | 20 | Hypertension, CFS, cytomegalic virus |
| 72, m | 5.00E+04 | 4.40E+04 | 4.70E+04 | −14.55 | hypertension, fatigue |
| 71, m | | 5.40E+04 | 6.60E+04 | 20 | hypertension, arthritis |
| 56, m | | 6.90E+04 | 7.10E+04 | 29.09 | hypertension, arthritis |

CAD = coronary artery disease,
CFS = chronic fatigue syndrome,
ASHD = atherosclerotic heart disease.

EXAMPLE 10

Source of Emission in Serum

Measurements of different fractions of fluorescent serum biomolecules were performed for identifying the different peaks in the serum emission spectrum derived from healthy volunteers and also for estimating the effect of different fluorescence components (proteins and coenzymes) on the native serum fluorescence. Others have shown that fluorescence of native serum can be attributed to a variety of molecules such as tryptophan (trp), tyrosine (tyr), phenylalanine (phe), ADH, pyridoxal phosphate, bilirubin, and flavin-adenine dinucleotide (FAD) (see Table 6). The components used in this analysis were: lyophilized albumin, human γ-globulin, 3-hydroxyanthranilic acid, 4-pyridoxic acid, pyridoxal-5-phosphate, and β-nicotinamide adenine dinucleotide (reduced form) (Sigma). The measured emission parameters for these fractions (excitation wavelength 315 nm) are shown in FIG. 3, the emission curves for the different fractions occurred at various wavelengths over the spectral region of native serum. To analyze the contribution of the different fractions to the emission of serum, the mathematical programming tool, Matlab, was used to solve a series of linear equations. The intensities of emission at a specific wavelength ($\lambda_i$) for the six different components with adjustable coefficients $A_n$, were summed to give the experimental emission intensity of the native serum at a specific wavelength. The curve fitting results indicated that the values for the coefficients of 3-hydroxyanthranilic acid, pyridoxal-5-phosphate and 4-pyridoxic acid were low and that the influence of emission from these fractions was negligible. The calculated curves for emission from other fractions (albumin, globulins, NADH) and their sum are shown in FIG. 3. As noted in FIG. 3, the calculated emission curve was in good agreement with the native fluorescence curve (average on graphs) and, hence, it may be described by emission of albumin, globulins and NADH in the 330–600 nm range.

$$\sum_{1}^{6} SEmission(\lambda i) = A_1 C_{NADH}(\lambda i) + A_2 C_{p-5-p}(\lambda i) +$$

$$A_3 C_{4-p-acid}(\lambda i) + A_i C_{3-h-acid}(\lambda i) + A_5 C_{alb}(\lambda i) + A_6 C_{glob}(\lambda i)$$

TABLE 6

Fluorescence intensity of different fractions of serum in visible and UV region

| analyzed fractions of serum | wavelength of maximum (nm) | emission range of half-intensity of emission (nm) |
|---|---|---|
| 3-hydroxyanthanilic acid[a] | 417 | 378–519 |
| 4-pyridoxic acid[a] | 429 | 395–485 |

TABLE 6-continued

Fluorescence intensity of different fractions of serum in visible and UV region

| analyzed fractions of serum | wavelength of maximum (nm) | emission range of half-intensity of emission (nm) |
|---|---|---|
| pyridoxal-5-phosphate[a] | 444 | 425–474 |
| nicotinamide adenine dinucleotide (NADH)[a] | 468 | 412–521 |
| serum proteins[b] | 342 | 312–379 |

[a]excitation by 315 nm wavelength:
[b]excitation by 280 nm wavelength

The possible reason for the changed serum emission for all groups of patients with metabolic disorders was analyzed. The main source of enzymes and coenzymes in serum may be from the storage of the NAD due to conversion of tryptophan and nicotinic acid, a process which is controlled by the liver in a hormone-sensitive manner. The enzymes and coenzymes in serum may also be due to leakage of these biomolecules after breakdown of the cells circulating in blood (red blood cells and white blood cells) and after breakdown of tissue cells. The tissue level of NAD+ may be regulated by the concentration of extracellular nicotinamide.

The question of whether the changed level of serum emission was due to decreased erythrocyte production associated with anemia or a decreased level of white blood cells due to pathological conditions was analyzed. For groups of patients (cancer, thyroid disorder, diabetes, fatigue arthritis) the laboratory tests of the complete blood count measurements on the same day of measurements of serum emission were compared with the parameters of serum emission. Part of the data for patients with cancer is presented in Table 7. The data presented in Table 7 demonstrated the changed level of serum emission and results of lab tests estimating the parameters of red cells (count, level of hemoglobin, hemotocrit, MCV (mean corpuscular volume), MCH (mean corpuscular hemoglobin), MCHC) and white cells with values for the normal range. This group of patients contained the highest number of cases with an abnormal blood count. The red blood cell and hemoglobin deficiencies may be observed in cancer patients for several reasons: blood loss, toxic depression of bone marrow, nutritional inadequacies, hemolysis, or the result of chemotherapy. Data presented in Table 7 also demonstrated that many cancer patients had changed levels of serum emission and a normal cell count as well as other parameters of PBC and WBC. The abnormalities in cell count and the level of hemoglobin were not observed with as much frequency for other groups of patients. A correlation between the red blood cell count, level of hemoglobin, MCH, MCV and white blood cell count with the level of serum emission at 470 nm was performed. There was practically no correlation between these parameters in all groups of patients or in a group of healthy volunteers. So, it was concluded that the reason for the changed level of serum emission (and possibly concentration of NAD(P)H in serum) may partially be due to a changed concentration of the cells which circulate in the bloodstream and migrate in tissue and release these biomolecules after breakdown. The changed level may also be due to the changed level of energy production and the changed level of metabolism in cells during the development of these pathological conditions, which may be associated with abnormalities of oxido-reductase enzymes.

TABLE 7

PARAMETERS OF SERUM EMISSION AND LABORATORY TESTS OF BLOOD COUNT FOR PATIENTS WITH CANCER

| patients age, sex | changed NADH | ratio of 430/470 | RBC 3.5–5.5 | hemoglobin 12.0–16 | hematocrit 34–48 | MCV 80–100 | MCH 26–34 | MCHC 31–37 |
|---|---|---|---|---|---|---|---|---|
| 38, f | −52.7 | 1.11 | 4.29 | 11.9 | 35.8 | 83.4 | 27.7 | 33.2 |
| 38, f | −11 | 0.89 | 4.25 | 13.6 | 37.8 | 89 | 32 | 36 |
| 42, f | −34.5 | 1.03 | 4.08 | 12.1 | 36 | 89 | 30 | 33 |
| 45, f | −14.5 | 0.89 | 3.54 | 12.1 | 35.7 | 100.8 | 34.2 | 339 |
| 45, f | −19 | 0.966 | 4.08 | 12.7 | 35.5 | 87.1 | 31.1 | 35.8 |
| 47, f | −11 | 0.98 | 4.46 | 14 | 41 | 91.9 | 31.4 | 34.1 |
| 45, f | −18.2 | 1.07 | 4.35 | 12.3 | 37.6 | 87 | 28 | 33 |
| 79, m | −36.4 | 1.114 | 3.25 | 10.1 | 30.3 | 93 | 31 | 33 |
| 73, f | −18.2 | 0.98 | 4.59 | 11.2 | 34.3 | 74.5 | 24.4 | 32.7 |
| 60, m | −7.3 | 0.92 | 4.34 | 12.5 | 40.1 | 92.5 | 31.8 | 34.4 |
| 67, f | −50.9 | 1.07 | 3.16 | 10.3 | 31 | 98 | 33 | 3 |
| 73, m | −29.1 | 0.95 | 4.53 | 13 | 38.7 | 86 | 29 | 34 |
| 51, m | −30 | 0.868 | 4.59 | 13.8 | 40.1 | 87.4 | 30.1 | 34.4 |
| 66, m | −36 | 1.114 | 3.1 | 10 | 29.5 | 95.2 | 32.3 | 33.9 |
| 51, m | −30.9 | 1.21 | 4.83 | 10.4 | 33 | 68.3 | 21.5 | 31.5 |
| 53, m | −12.7 | 0.916 | 4.63 | 12.5 | 37.7 | 81.5 | 27 | 33.2 |
| 68, m | −20 | 0.886 | 5.09 | 15.4 | 43.6 | 85.7 | 30.3 | 35.3 |
| 73, m | −36.4 | 1.010 | 3.96 | 12.8 | 35.8 | 90 | 32.2 | 35.8 |
| 55, m | −20 | 1.045 | 4.6 | 14.3 | 41 | 89 | 31 | 35 |
| 70, m | −9.1 | 1.04 | 4.58 | 15.1 | 44 | 96.1 | 33 | 34.3 |
| 46, m | −45 | 1.067 | 4.62 | 15.1 | 43.1 | 93 | 33 | 35 |
| 86, m | −21.8 | 1.023 | 3.81 | 12.4 | 35 | 92 | 33 | 35 |
| 47, f | −45.4 | 1.005 | 5.35 | 14.9 | 43.4 | 81.1 | 27.9 | 34.3 |
| 65, f | −12.7 | 0.979 | 3.17 | 11 | 32.8 | 104 | 35 | 34 |
| 74, f | −61.8 | 1.14 | 4.06 | 11.1 | 33.4 | 82 | 27 | 33 |
| 39, f | −49 | 1.07 | 3.24 | 10.6 | 31.8 | 98 | 33 | 33 |
| 54, f | −40 | 1.03 | 4.73 | 14.2 | 42 | 88.7 | 30 | 33.8 |
| 59, m | −13.6 | 1.01 | 3.01 | 10.1 | 30.2 | 100.3 | 33.6 | 33.4 |
| 47, f | −36 | 0.97 | 4.4 | 14.4 | 41 | 93 | 33 | 35 |

TABLE 7-continued

PARAMETERS OF SERUM EMISSION AND LABORATORY
TESTS OF BLOOD COUNT FOR PATIENTS WITH CANCER

| patients age, sex | changed NADH | ratio of 430/470 | RBC 3.5–5.5 | hemoglobin 12.0–16 | hematocrit 34–48 | MCV 80–100 | MCH 26–34 | MCHC 31–37 |
|---|---|---|---|---|---|---|---|---|
| 42, f | −23 | 1.047 | 3.74 | 11.8 | 35.7 | 95 | 32 | 33 |
| 63, m | −44 | 0.998 | 4.16 | 13.7 | 40.7 | 98 | 33 | 34 |

For example, for the highest population of cells in blood, the red blood cells, energy production which depends on glycolysis (with glucose as the principal substrate), may influence the level of NAD(P)H. Glycolysis and the oxidative pentose pathway generate NADH and NADPH to reduce both methemoglobin, which is being continuously produced, and the antioxidant glutathione, which is present in high concentrations. A correlation was identified between ATP and pyridine cofactors in cells. Changes in the NADH level and NAD redox potential (ratio of NADH to $NAD^++NADH$) and a decreased NAD redox potential and NADH level in cells was found for patients with a variety of pathological conditions and was found to correlate with a decreased level of enzymes. It was demonstrated that NAD synthesis was impaired as was adenosine-5'-triphosphate (ATP) concentration in these cells. In addition, the levels of ATP, ADP, NADP, NADPH, NAD, NADH were analyzed for patients with a glucose-6-phosphate dehydrogenase (G6PD) deficiency and it was concluded that the deficiency caused a reduced concentration of NADPH.

For all abnormal serum emission samples for patients with pathological conditions the changed level of emission at 470 nm and changed ratio of fluorescence emission at 430 nm to 470 nm may be the reason for the changed level of energy production in cells and may be the reason for the changed level of enzymes and abnormalities of the oxidoreductase system.

A change in metabolism was commonly observed in various diseases such as diabetes, thyroid disorder, AIDS, cancer and others as measured by serum emission. The level of metabolic activity increased with some conditions (hypermetabolic response) or decreased with others (hypometabolic response). Thus, this method can be used to screen a patient during a yearly exam or physical to identify a possible abnormality which has not presented as symptomatic. In example 10 a method is provided to screen a patient.

EXAMPLE 11

Initial Blood Serum Screening

For some patients, a hypometabolic or a hypermetabolic response may indicate that the patient is at risk for organ failure or morbidity. Thus, a method to routinely determine a patient's energy level would be helpful for risk assessment. A non-invasive methodology has been designed herein to estimate the level of energy metabolism by measuring the fluorescence of reduced nicotinamide adenine dinucleotide (NADH) as well as other fluorescing molecules in serum. A serum sample is obtained from a patient who has fasted for 8 to 24 hours. The sample is irradiated at an irradiation wavelength from about 300 to about 340 nm. The serum emission is measured at a wavelength from about 300 to about 600 nm; and the patient is diagnosed as having a metabolic dysfunction by an increased or decreased emission in comparison to an average emission at the same wavelength of serum of a plurality of normal healthy volunteers.

EXAMPLE 12

A Method to Monitor the Metabolic State of a Patient

A procedure for serial sampling to monitor the metabolic state of patients under intensive care during critical illnesses is presented. The method may be used to establish the efficacy of a treatment or could be used to monitor the "health state" of a patient to determine if the patient is capable of undergoing a difficult procedure, such as surgery.

A first sample of serum is obtained before the treatment of a patient. The serum is obtained from the patient who has fasted for at least 8 hours. The first sample is irradiated at an irradiation wavelength from about 300 to about 340 nm; and the serum emission of the sample is measured at an emission wavelength from about 300 to about 600 nm. Second and subsequent samples are obtained at different time points or before and after treatment. The effectiveness of the treatment is diagnosed by an increased or decreased emission in the second sample relative to the first sample. Alternatively, the "health state" of the patient is diagnosed by an increased or decreased emission. In the case of cancer, an effective treatment will show an increased emission.

Summary

In summary, all populations of data, which were analyzed for patients with different metabolic disorders, showed characteristic changes in serum emission for patients from different groups of chronic diseases. The level of emission outside the normal range was recorded for 50% of patients with thyroid disorder, 56% in patients with diabetes, 80% in patients with CAD and hypertension, 55% with arthritis, 50% in patients with fatigue and fibromyalgia. The most significant data was identified for patients with cancer. For this pathological condition, the study indicates that the level of serum emission is lower than the same parameters for healthy volunteers.

Other variations of the preferred embodiments will be apparent to one of skill in the art with reference to the following claims.

What is claimed is:

1. A method for the diagnosis of a disease of metabolic dysfunction, comprising:
   obtaining a sample of serum from a patient;
   irradiating the sample with a plurality of irradiation wavelengths from about 300 to about 340 nm simultaneously;
   measuring the serum emission at one or more wavelengths from about 300 to about 600 nm; and
   diagnosing the presence of a metabolic dysfunction by an increased or decreased emission in comparison to an average emission at said wavelength of serum of a plurality of normal healthy volunteers.

2. The method of claim 1 wherein said emission wavelength is from about 330 to about 550.

3. The method of claim 1 wherein said emission wavelength is from about 370 to about 550.

4. The method of claim 1 wherein said emission wavelength is from about 425 to about 500.

5. The method of claim 1 wherein said emission wavelength is from about 470 to about 500.

6. The method of claim 1 wherein said emission wavelength is from about 460 to about 490.

7. The method of claim 1 wherein said plurality of irradiation wavelengths is selected from the group consisting of: 315, 325 and 340.

8. The method of claim 1 wherein said metabolic dysfunction is cancer and the serum emission is reduced.

9. The method of claim 8 wherein a patient with cancer has more than a 5% decrease in the level of serum emission.

10. The method of claim 8 wherein a patient with cancer has more than a 10% decrease in the level of serum emission.

11. The method of claim 8 wherein a patient with cancer has more than a 20% decrease in the level of serum emission.

12. The method of claim 8 wherein a patient with cancer has a decrease in the serum emission from about 5% to about 60%.

13. The method of claim 8 wherein a patient with cancer has a decrease in the serum emission from about 10% to about 50%.

14. The method of claim 8 wherein said cancer is selected from the group consisting of: breast cancer, lung cancer, colon cancer, prostate cancer and leukemia.

15. The method of claim 1 wherein said metabolic dysfunction is hypothyroidism and the serum emission is reduced.

16. The method of claim 1 wherein said metabolic dysfunction is hyperthyroidism and the serum emission is increased.

17. The method of claim 1 wherein said metabolic dysfunction is diabetes and the serum emission is reduced.

18. The method of claim 1 wherein said metabolic dysfunction is fatigue and the serum emission is reduced.

19. The method of claim 1 wherein said metabolic dysfunction is coronary artery disease (CAD) and the serum emission is reduced.

20. The method of claim 1 wherein said sample is irradiated at both 325 nm and 340 nm.

21. The method of claim 1, wherein said sample is irradiated at the wavelength which allows the best resolution for NAD(P)H.

22. The method of claim 1 wherein said patient has fasted for more than about 8 hours before the sample is taken.

23. The method of claim 1, wherein said patient has fasted for about 2 to about 24 hours before the sample is taken.

24. The method of claim 23, wherein said patient has fasted for about 8 to about 12 hours before the sample is taken.

25. The method of claim 24, wherein said patient has fasted for about 10 to about 12 hours before the sample is taken.

26. A method for analysis of the effectiveness of a treatment, comprising:
   obtaining a first sample of serum from a patient before the treatment;
   irradiating the first sample at more than one irradiation wavelength from about 300 to about 340 nm simultaneously;
   measuring the serum emission at at least one emission wavelength from about 300 to about 600 nm;
   obtaining a second sample of serum from a patient after the treatment, wherein said patient has fasted for at least about 8 hours prior to obtaining the first sample;
   irradiating the second sample at more than one irradiation wavelength from about 300 to about 340 nm simultaneously;
   measuring the serum emission at at least one emission wavelength from about 300 to about 600 nm; and
   diagnosing the effectiveness of the treatment by an increased or decreased emission in the second sample relative to the first sample.

27. The method of claim 26, wherein the treatment is a treatment for cancer and the treatment is diagnosed as being effective by an increased emission.

28. The method of claim 26, wherein said patient has fasted for at least about 8 hours prior to obtaining the first and subsequent samples.

29. The method of claim 26, wherein said patient has fasted for at least about 2 hours prior to about 24 hours before obtaining the first and subsequent samples.

30. The method of claim 26, wherein said patient has fasted for at least about 6 hours prior to about 12 hours before obtaining the first and subsequent samples.

31. The method of claim 26 wherein said emission is measured at more than one emission wavelength simultaneously.

* * * * *